United States Patent [19]
Heintz et al.

[11] Patent Number: 6,143,566
[45] Date of Patent: Nov. 7, 2000

[54] METHODS OF PERFORMING HOMOLOGOUS RECOMBINATION BASED MODIFICATION OF NUCLEIC ACIDS IN RECOMBINATION DEFICIENT CELLS AND USE OF THE MODIFIED NUCLEIC ACID PRODUCTS THEREOF

[75] Inventors: Nathaniel Heintz, Pelham Manor; Peter Model; Xiangdong W. Yang, both of New York, all of N.Y.

[73] Assignee: The Rockfeller University, New York, N.Y.

[21] Appl. No.: 08/880,966

[22] Filed: Jun. 23, 1997

[51] Int. Cl.⁷ .................................................. C12N 15/87
[52] U.S. Cl. ........................ 435/463; 435/440; 435/455; 435/465; 435/466; 435/320.1
[58] Field of Search ................................. 435/4, 6, 440, 435/455, 463, 465, 466

[56] References Cited

FOREIGN PATENT DOCUMENTS 0742285 11/1996 European Pat. Off. .
WO 97/29202 8/1997 WIPO .

OTHER PUBLICATIONS

Balasubramanian et al., *J. of Bacteriology* 178:273–279 (1996).
Birnboim et al., *Nucleic Acids Res.* 7:1513–1523 (1979.
Bochner et al., *J. Bacteriol.* 143:926–33 (1980).
Boyseu et al., *Genome Research*, 7:330–338 (1997).
Bradley et al., *Nature Genet.* 14:121–3 (1997).
Brinster et al. (1989) *Proc.Natl.Acad.Sci.* 86:7087–91.
Brinster et al., *Proc.Natl.Acad.Sci.* 85:836–840 (1988).
Burke et al., *Science* 236:806–12.
Clark et al., *Critical Reviews in Microbiology* 20:125–142 (1994).
Deng and Capecchi (*MCB*, 12:3365–3371).
Dillon et al., *Trends Genet.* 9:134–7 (1993).
Fujitani et al. (1995) Genetics 140:797–809.
Gnirke et al. (1993) Genomics 15:659–67.
Hamilton et al., *J. Bacteriol.* 171:4617–22 (1989).
Harrington et al. *Nature Genetics*, 15:345–355 (1997).
Hashimoto–Gotoh et al. (1977) J. Bacteriol. 131:405–12.
Hosoda et al., *Nucleic Acids Res.* 18:3863–9 (1990).
Ioannou et al., *Nat. Genet.*, 6:84–89 (1994).
Jaenisch et al., *Science* 240:1468–74 (1985).
Joyner, A., Ed. *Gene Targeting, a practical approach*, IRL Press: Oxford, New York, Tokyo Table of Contents Only Provided.
Kennison, *Trends Genet.* 9:75–9 (1993).
Kim et al. *MCB*, 12:3636–3643 (1992).
Kim et al., *Proc.Natl.Acad.Sci.* 93:6297–6301 (1996).
Kuhn et al., *Science* 269:1427–9 (1995).
Maloy et al., *Bacteriol.* 145:1110 (1981).
McKee et al., *Chromosoma* 7:479–488 (1996).
Mejia et al., *Genome Res.* 7:179–186 (1997).
Monaco et al., *Trends Biotechnol* 12:280–286 (1994).
O'Connor et al. *Science*, 244:1307–1312 (1989).
Palmiter et al., *Cell* 41:343–5 (1985).
Peakman et al., *Proc.Natl.Acad.Sci.* 93:10222–10227 (1996).
Peterson et al., *TIG* (*Trends Genet.*) 13:61–66 (1997).
Reiss et al.,*Proc.Natl.Acad.Sci.* 93:3094–3098 (1996).
Shizuya et al., Proc. Natl. Acad. Sci. 89:8794–8797 (1992).
Spencer et al. (1993) Meth.: Comp. Meth. Enzymol. 5:161–75.
Tsien et al., *Cell* 87:1317–26 (1996).
Wang et al., *Genomics* 24:527–34 (1994).
Wilson et al., *Annu.Rev.Cell.Biol.* 6:679–714 (1990).
Woo et al., *Nucleic Acids Res.*, 22:4922–31 (1994).
Wooster et al., *Nature* 378:789–92 (1995).
Yang et al., *Development* 122:555–66 (1996).
Hosoda et al. Nucleic Acids Research. vol. 18, No. 13, pp. 3863–3869, 1990.
Ioannou et al. Nature Genetics. vol. 6, pp. 84–89, Jan. 1994.
Shizuya et al. Nucleic Acids Research. vol. 22, No. 22, pp. 4922–4931, 1994.
Wo et al. Proc. Nat'l. Acad. Sci. U.S.A. vol. 89, pp. 8794–8797, 1992.
Baker & Cotten, Nucleic Acids Research 25: 1950–1956 (1997).
Chatterjee & Cohen, Nucleic Acids Research 25:2205–2212 (1997).

*Primary Examiner*—Remy Yucel
*Attorney, Agent, or Firm*—Klauber & Jackson

[57] ABSTRACT

A simple method for modifying genes in a recombination deficient host cell is disclosed. Such modifications include generating insertion, deletions, substitutions, and/or point mutations at any chosen site in the independent origin based cloning vector. The modified gene can be contained in an independent origin based cloning vector that is used to introduce a modified heterologous gene into a cell. Such a modified vector may be used in the production of a germline transmitted transgenic animal, or in gene targeting protocols in eukaryotic cells.

50 Claims, 10 Drawing Sheets

FIG. 1
I. Construction of the recA(+) and temperature sensitive shuttle vector
1) Clone two small genomic fragments (> 500 bp each) into the building vector (pBV1)
2) Transfer the recombination cassette into the Ts-RecA(+) shuttle vector (pSV1.RecA)
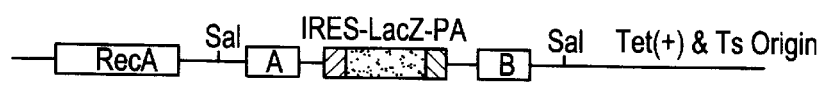
II. Transformation of the shuttle vector into the E.Coli host strain of BACs and selection for co-integrates
III. Resolution
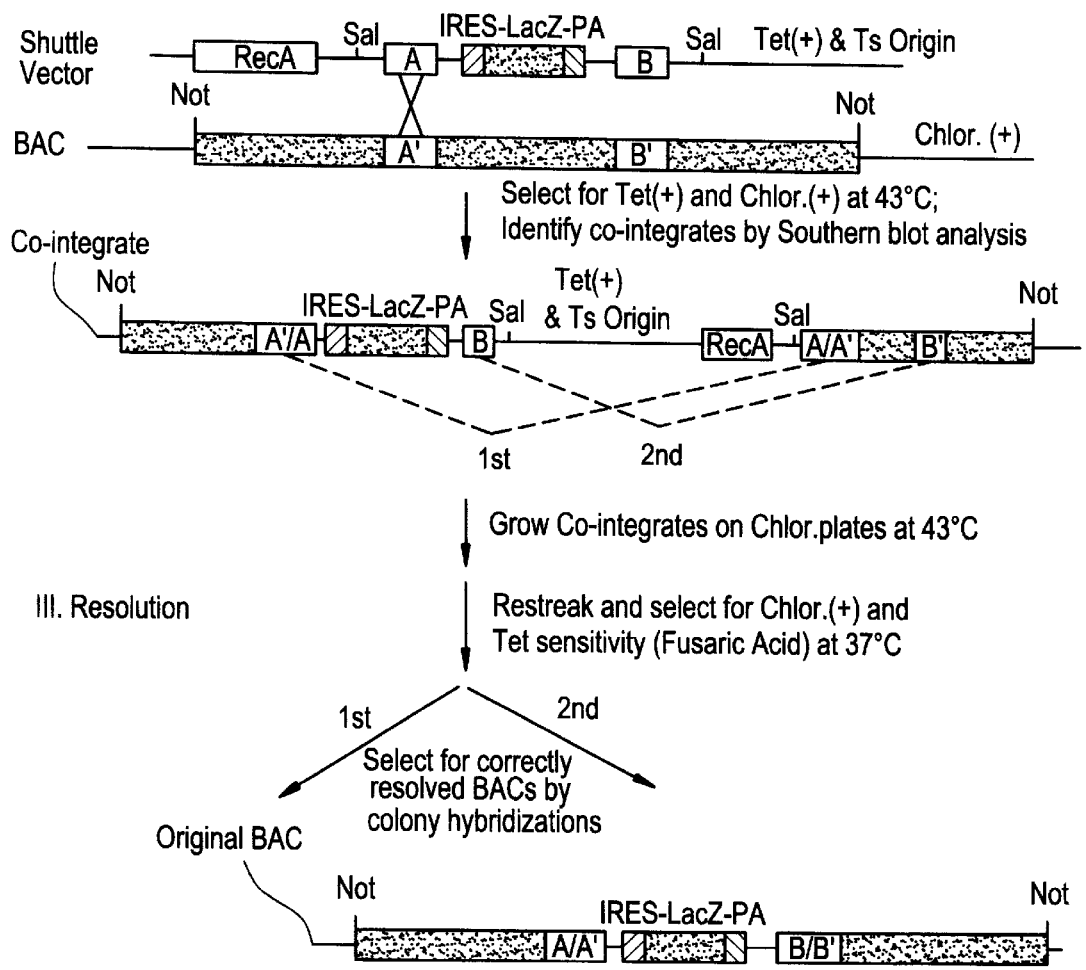

Map of the RU49 Genomic Locus within BAC169

Map of the Modifified BAC 169 with an IRES-LacZ-PolyA Insertion

FIG. 7A
Hypothetical map of a gene of interest within a selected BAC (>150kb insert size)

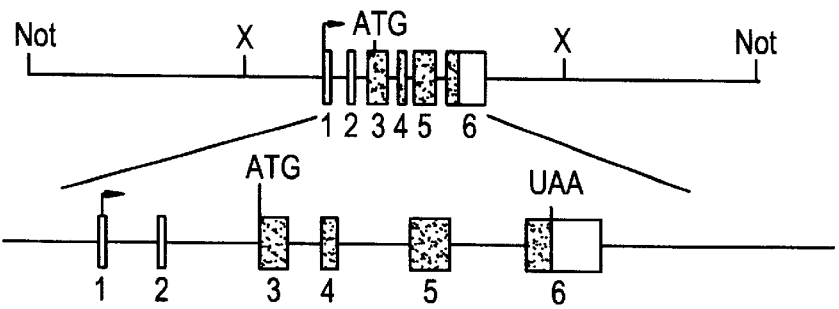

FIG. 7B
First targeted modification to introduce the positive selection marker gene

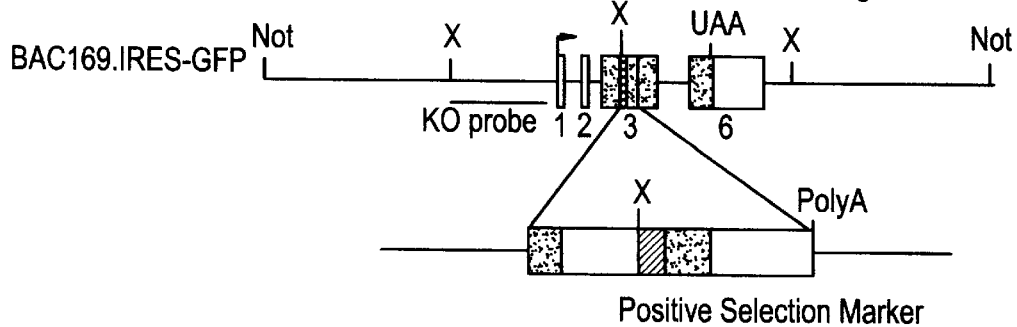

ES Cells Targeting: Marker gene=PGK-Neo-PA
Transgenic knock-out: Marker gene=IRES-EGFP-1 or IRES-LacZ

FIG. 7C
Second Modification to delete the promoter of the gene and to generate the short arm

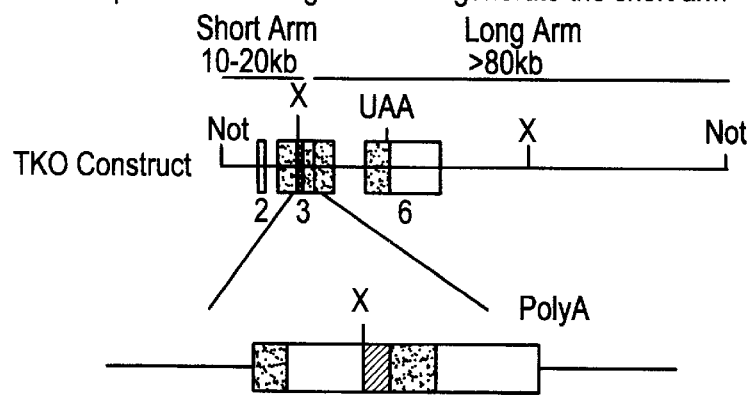

Selection of positive clones by Southern blots:
Digest DNA with enzyme X and probed with the KO probe
  Endogenous allele: >50kb
  Target allele: <20kb

METHODS OF PERFORMING HOMOLOGOUS RECOMBINATION BASED MODIFICATION OF NUCLEIC ACIDS IN RECOMBINATION DEFICIENT CELLS AND USE OF THE MODIFIED NUCLEIC ACID PRODUCTS THEREOF

GOVERNMENTAL SUPPORT

The research leading to the present invention was supported, at least in part, by a grant from the National Science Foundation Grant No. MCB-9316625. Accordingly, the Government may have certain rights in the invention.

FIELD OF THE INVENTION

This invention relates generally to methods of modifying genes with specificity in recombination deficient cells by transiently enabling homologous recombination in the cells. Included in the invention are conditional replication shuttle vectors which bestow transient recombination capabilities to an otherwise recombination deficient cell. The independent origin based cloning vectors containing the modified genes and methods of using the independent origin based cloning vectors containing the modified genes are also included in the present invention.

BACKGROUND OF THE INVENTION

Functional analyses of genes in vivo frequently involve the introduction of modified genomic DNA into the germline to generate transgenic animals [Jaenisch et al., Science 240:1468 (1985); Brinster, Cell 41:343 (1985)]. The genomic DNA sequences containing introns and essential regulatory sequences have been shown to be expressed in vivo in cases where simple cDNA constructs cannot be expressed [Brinster et al., Proc. Natl. Acad. Sci. 85:836–840 (1988)]. Furthermore, the size of the genomic DNA that can be readily manipulated in vitro and introduced into the germline can be a critical determinant of the outcome of the functional analysis of a gene since elements that are important for high level, tissue specific and position-independent expression of the transgene may be located at a long distance from the gene itself [Dillon et al., Trends Genet. 9:134 (1993); Kennison, Trends Genet. 9:75 (1993); Wilson et al., Annu. Rev. Cell. Biol. 6:679 (1990)].

On the other hand, the use of such large genomic transgenes has several practical problems. For example, the size of the transgene is presently limited due to constraints on the sequence length that can be cloned and stably maintained in a conventional plasmid or a cosmid. Thus DNA sequences suspected of being nonessential are often omitted when designing the constructs to be transferred because of the size limitation. In addition, in vitro manipulations of large DNAs oftentimes lead to mechanical shear [Peterson et al., TIG 13:61–66].

Yeast artificial chromosomes (YACs) allow large genomic DNA to be modified and used for generating transgenic animals [Burke et al., Science 236:806; Peterson et al., Trends Genet. 13:61 (1997); Choi, et al., Nat. Genet., 4:117–223 (1993), Davies, et al., Biotechnology 11:911–914 (1993), Matsuura, et al., Hum. Mol. Genet., 5:451–459 (1996), Peterson et al., Proc. Natl. Acad. Sci., 93:6605–6609 (1996); and Schedl, et al., Cell, 86:71–82 (1996)]. Other vectors also have been developed for the cloning of large segments of mammalian DNA, including cosmids, and bacteriophage P1 [Sternberg et al., Proc. Natl. Acad. Sci. U.S.A., 87:103–107 (1990)]. YACs have certain advantages over these alternative large capacity cloning vectors [Burke et al., Science, 236:806–812 (1987)]. The maximum insert size is 35–30 kb for cosmids, and 100 kb for bacteriophage P1, both of which are much smaller than the maximal insert for a YAC. However, there are several critical limitations in the YAC system including difficulties in manipulating YAC DNA, chimerism and clonal instability [Green et al., Genomics, 11:658 (1991); Kouprina et al., Genomics 21:7 (1994); Larionov et al., Nature Genet. 6:84 (1994)]. As a result, generating transgenic mice with an intact YAC remains a challenging task [Burke et al., Science 236:806; Peterson et al., Trends Genet. 13:61 (1997)].

An alternative to YACs are E. coli based cloning systems based on the E. coli fertility factor that have been developed to construct large genomic DNA insert libraries. They are bacterial artificial chromosomes (BACs) and P-1 derived artificial chromosomes (PACs) [Mejia et al., Genome Res. 7:179–186 (1997); Shizuya et al., Proc. Natl. Acad. Sci. 89:8794–8797 (1992); Ioannou et al., Nat. Genet., 6:84–89 (1994); Hosoda et al., Nucleic Acids Res. 18:3863 (1990)]. BACs are based on the E. coli fertility plasmid (F factor); and PACs are based on the bacteriophage P1. The size of DNA fragments from eukaryotic genomes that can be stably cloned in Escherichia coli as plasmid molecules has been expanded by the advent of PACs and BACs. These vectors propagate at a very low copy number (1–2 per cell) enabling genomic inserts up to 300 kb in size to be stably maintained in recombination deficient hosts (most clones in human genomic libraries fall within the 100–200 kb size range). The host cell is required to be recombination deficient to ensure that non-specific and potentially deleterious recombination events are kept to a very minimum. As a result, libraries of PACs and BACs are relatively free of the high proportion of chimeric or rearranged clones typical in YAC libraries, [Monaco et al., Trends Biotechnol 12:280–286 (1994); Boyseu et al., Genome Research, 7:330–338 (1997)]. In addition, isolating and sequencing DNA from PACs or BACs involves simpler procedures than for YACs, and PACs and BACs have a higher cloning efficiency than YACs [Shizuya et al., Proc. Natl. Acad. Sci. 89:8794–8797 (1992); Ioannou et al., Nat. Genet., 6:84–89 (1994); Hosoda et al., Nucleic Acids Res. 18:3863 (1990)]. Such advantages have made BACs and PACs important tools for physical mapping in many genomes [Woo et al., Nucleic Acids Res., 22:4922 (1994); Kim et al., Proc. Natl. Acad. Sci. 93:6297–6301 (1996); Wang et al., Genomics 24:527 (1994); Wooster et al., Nature 378:789 (1995)]. Furthermore, the PACs and BACs are circular DNA molecules that are readily isolated from the host genomic background by classical alkaline lysis [Birnboim et al., Nucleic Acids Res. 7:1513–1523 (1979].

Functional characterization of a gene of interest contained by a PAC or BAC clone generally entails transferring the DNA into a eukaryotic cell for transient or long-term expression. A transfection reporter gene, e.g., a gene encoding lacZ, together with a selectable marker, e.g., neo, can be inserted into a BAC [Mejia et al., Genoine Res. 7:179–186 (1997). Transfected cells can be then detected by staining for X-Gal to verify DNA uptake. Stably transformed cells are selected for by the antibiotic G418.

However, while PACs and BACs have cloning capacities up to 350 kb, performing homologous recombination to introduce mutations into a gene of interest has not been demonstrated [Peterson et al., TIG 13:61–66]. Indeed, although BACs or PACs have become an important source of large genomic DNA in genome research, there are still no methods available to modify the BACs or PACs.

Furthermore, no germline transmission of intact BACs or PACs in transgenic mice have been reported. These, as well as other disadvantages of BACs and PACs greatly limit their potential use for functional studies. Therefore, there is a need for an improved cloning vector for germline transmission of selected genes in transgenic animals. More particularly there is a need for a cloning vector that has the capacity to contain greater than 100 kilobases of DNA, which can be readily manipulated and isolated, but still can be stably stored in libraries relatively free of rearranged clones. In addition, there is a need to provide methodology for generating such cloning vectors. There is also a need to apply such vectors to improve current technologies such as gene targeting.

Gene targeting has been used in various systems, from yeast to mice, to make site specific mutations in the genome. Gene targeting is not only useful for studying function of proteins in vivo, but it is also useful for creating animal models for human diseases, and in gene therapy. The technique involves the homologous recombination between DNA introduced into a cell and the endogenous chromosomal DNA of the cell. However, in the vertebrate system, the rate of homologous recombination is very low, as compared to random integration. The only cell line that allows a relatively high homologous recombination rate and maintains the ability to populate the germline is the murine 129 embryonic stem cells (ES cells). Using this specialized cell, mice can be generated with a targeted mutation (*Gene Targeting, a practical approach* Ed. by A. Joyner, IRL Press: Oxford, New York, Tokyo). However, the rate of homologous recombination for some gene loci in ES cells is still extremely low (<1%), the procedure is labor intensive, and the cost of generating targeted mutant mice is very expensive. Moreover, since there are no ES cells available for vertebrates other than mice, gene targeting in a germline is still not possible for other vertebrates.

The major limitation for gene targeting in vertebrate cells remain to be the low targeting frequency. One critical factor affecting the targeting frequency is the total length of homology. Deng and Capecchi (*MCB*, 12:3365–3371) have shown that gene targeting frequency is linearly-dependent on the logarithm of the total homology length over homology lengths of 2.8 kb to 14.6 kb. Since the curve did not plateau at the 14.6 kb homology, it is likely that incorporating greater homology lengths into the targeting vector will further increase the homologous recombination rate. Using a mathematical model developed by Fujitani et al, [*Genetics*, 140:797–809, (1995)], an estimate can be made that with a total homology of 100 kb isogenous DNA (i.e., DNA from the same strain of mice), the gene targeting rate in ES cells would be 10%. This is a dramatic improvement over the conventional 14.6 kb targeting vector, which only yields a corresponding rate of only 0.03%. Further support for the present strategy i.e., using a large DNA construct for gene targeting rate comes from an experiment with Mycobacterium tuberculosis, the causal agent of tuberculosis. Like vertebrate cells, gene targeting in TB has a very low rate, mainly due to the predominance of random integration over homologous recombination. It has been demonstrated that using a 40–50 kb linear targeting construct, a 6% targeting frequency could be obtained, whereas no targeting event was obtained at all with a smaller (<10 kb) targeting construct [Balasubramanian et al., *J. of Bacteriology* 178:273–279 (1996)]. Therefore, there is a need to construct large gene targeting constructs to allow efficient gene targeting in many biological systems.

The citation of any reference herein should not be construed as an admission that such reference is available as "Prior Art" to the instant application.

SUMMARY OF THE INVENTION

The present invention provides a novel and efficient method of modifying independent origin based cloning vectors for in vitro and in vivo gene expression. In its broadest embodiment, the present invention provides a method of selectively performing homologous recombination on a particular nucleotide sequence contained in a recombination deficient host cell, i.e., a cell that cannot independently support homologous recombination. The method employs a recombination cassette which contains a nucleic acid that selectively integrates into the particular nucleotide sequence when the recombination deficient host cell is induced to support homologous recombination. The method comprises introducing the recombination cassette into the recombination deficient host cell, and inducing the recombinantly deficient host cell to transiently support homologous recombination, thereby allowing the nucleic acid to integrate into the particular nucleotide sequence. In a preferred embodiment, unselected nucleotide sequence rearrangements and deletions, which are characteristic of host cells that support homologous recombination, are not evident with restriction endonuclease digestion map analysis with a restriction enzyme such as HindIII, EcoRI, XhoI, or AvrII. In a more preferred embodiment, unselected nucleotide sequence rearrangements and deletions are not evident with restriction endonuclease digestion map analysis with two or more restriction enzymes.

In a particular aspect of the present invention, the recombination deficient host cell cannot independently support homologous recombination because the host cell is RecA$^-$. In this aspect of the invention, inducing the host cell to transiently support homologous recombination comprises inducing the transient expression of a RecA-like protein in the host cell. In a preferred embodiment, inducing the transient expression of the RecA-like protein can be performed with a conditional replication shuttle vector. In a more preferred embodiment the conditional replication shuttle vector is a temperature sensitive shuttle vector (TSSV) that replicates at a permissive temperature, but does not replicate at a non-permissive temperature.

In one particular embodiment of this type, inducing the transient expression of the RecA-like protein comprises transforming the host cell with the TSSV at a permissive temperature, and growing the host cell at a non-permissive temperature. The TSSV encodes a RecA-like protein that is expressed in the host cell and supports the homologous recombination between a nucleic acid contained in a recombination cassette and the particular nucleotide sequence contained in the host cell. The TSSV encoding the RecA-like protein is diluted out when the host cell is grown at the non-permissive temperature. In one particular embodiment of this type the permissive temperature is 30° C. and the non-permissive temperature is 43° C.

In a more intricate version of the present invention, the particular nucleotide sequence which has been selected to undergo homologous recombination is contained in an independent origin based cloning vector (IOBCV) that is comprised by the host cell, and neither the independent origin based cloning vector alone, nor the independent origin based cloning vector in combination with the host cell, can independently support homologous recombination. In a particular embodiment of this type both the independent origin based cloning vector and the host cell are RecA$^-$, and inducing the host cell to transiently support homologous recombination comprises inducing the transient expression of the RecA-like protein to support homologous recombination in the host cell. In one particular embodiment the independent origin based cloning vector is a Bacterial or Bacteriophage-Derived Artificial Chromosome (BBPAC) and the host cell is a host bacterium.

In a preferred embodiment, inducing the transient expression of the RecA-like protein is performed with a conditional replication shuttle vector that encodes the RecA-like protein. In a more preferred embodiment the conditional replication shuttle vector is a temperature sensitive shuttle vector (TSSV) that replicates at a permissive temperature, but does not replicate at a non-permissive temperature. In one particular embodiment of this type the permissive temperature is 30° C. and the non-permissive temperature is 43° C.

In one embodiment the RecA-like protein is controlled by an inducible promoter and the transient expression of the RecA-like protein is achieved by the transient induction of the inducible promoter in the host cell. In another embodiment, the RecA-like protein is controlled by a constitutive promoter with the transient expression induced by the TSSV.

In a preferred embodiment the TSSV also comprises a recombination cassette and a first gene which bestows resistance to a host cell that contains the TSSV against a first toxic agent. In addition, the first gene can be counter-selected against. The recombination cassette, the RecA-like protein gene, and the first gene are linked together on the TSSV such that when the nucleic acid integrates (i.e. resolved) into the particular nucleotide sequence, the RecA-like protein gene and the first gene remain linked together, and neither the RecA-like protein gene nor the first gene remain linked to the integrated nucleic acid.

In a particular embodiment of this type, the independent origin based cloning vector is a BBPAC and the host cell is a bacterium. The BBPAC further contains a second gene that bestows resistance to the host cells against a second toxic agent. Introducing the recombination cassette into the host cells is performed by transforming the host cell with the TSSV. Inducing the transient expression of the RecA-like protein to support homologous recombination comprises: (i) incubating the host cells at a permissive temperature in the presence of the first toxic agent and the second toxic agent, wherein transformed host cells containing the TSSV and the BBPAC are selected for and wherein the RecA-like protein is expressed. A first homologous recombination event occurs between the recombination cassette and the particular nucleotide sequence forming a co-integrate between the TSSV and the BBPAC, wherein the TSSV is either free or part of a co-integrate; (ii) incubating the transformed host cells at a non-permissive temperature in the presence of the first toxic agent and the second toxic agent, wherein host cells containing a TSSV co-integrate are selected for, and wherein free TSSV cannot replicate; (iii) selecting a host cell containing a co-integrate between the TSSV and the BBPAC by Southern analysis; (iv) incubating the host cells containing a co-integrate between the TSSV and the BBPAC at a non-permissive temperature in the presence of the second toxic agent, wherein a second homologous recombination event occurs between the recombination cassette and the particular nucleotide sequence, therein integrating the nucleic acid into the particular nucleotide sequence and forming a resolved host cell, i.e., a host cell containing a resolved BBPAC; and (v) incubating the host cells containing the resolved BBPAC in the presence of the second toxic agent, and a counter-selecting agent, and wherein the counter-selecting agent is toxic to host cells containing the first gene, and wherein host cells containing the RecA-like protein gene are removed. Another embodiment further comprises selecting a host cell containing the resolved BBPAC by colony hybridization with a labeled probe that binds to a DNA homologue of the nucleic acid, an mRNA homologue of the nucleic acid, and/or a protein encoded by the nucleic acid. In a particular embodiment, the permissive temperature is 30° C., the non-permissive temperature is 43° C. In a preferred embodiment the incubating of host cells containing the resolved BBPAC in the presence of the second toxic agent and counter-selecting agent is performed at 37° C.

Preferred embodiments further comprise the generating of the recombination cassette by placing a first genomic fragment 5' of the specific nucleic acid that is to selectively integrate into the particular nucleotide sequence, and placing a second genomic fragment 3' of the specific nucleic acid. The first genomic fragment corresponds to a region of the particular nucleotide sequence that is 5' to the region of the particular nucleotide sequence that corresponds to the second genomic fragment. In one such embodiment, both the first genomic fragment and the second genomic fragment contain 500 or more basepairs of the particular nucleotide sequence. In a preferred embodiment, the first and second genomic fragments are about the same size. In another embodiment, both the first genomic fragment and the second genomic fragment contain 1000 or more basepairs of the particular nucleotide sequence. In one particular embodiment the recombination cassette is generated in a building vector and the recombination cassette is subsequently transferred to the TSSV.

In a particular embodiment the first gene confers tetracycline resistance and the counter-selecting agent is fusaric acid. In a preferred embodiment the RecA-like protein is recA. In the more preferred embodiment the TSSV is pSV1.RecA having the ATCC no. 97968.

In a related aspect of the present invention the RecA-like protein is controlled by an inducible promoter, and the transient expression of the RecA-like protein is achieved by the transient induction of the inducible promoter in the host cell. In one embodiment of this type, the independent origin based cloning vector is a BBPAC and the recombination deficient host cell is an *E. coli* bacterium. In a preferred embodiment the RecA-like protein is recA.

The present invention also provides a conditional replication shuttle vector that encodes a RecA-like protein. In one such embodiment the RecA-like protein is controlled by an inducible promoter. In a preferred embodiment the conditional replication shuttle vector is a temperature sensitive shuttle vector (TSSV). The RecA-like protein of the TSSV can be controlled by either a constitutive promoter or by an inducible promoter. In one embodiment the TSSV contains a gene that can be counter-selected against. In a specific embodiment of this type the TSSV contains a gene that confers tetracycline resistance. In another embodiment the TSSV contains a RecA-like protein that is recA. In still another embodiment the TSSV contains both a gene that confers tetracycline resistance and a RecA-like protein that is recA. In a preferred embodiment the TSSV is pSV1.RecA having the ATCC no. 97968.

The present invention also provides an independent origin based cloning vector that contains a particular nucleotide sequence that has undergone homologous recombination with a conditional replication shuttle vector in a RecA-host cell, wherein the conditional replication shuttle vector encodes a RecA-like protein. In one such embodiment the particular nucleotide sequence is part of the gene that encodes the murine zinc finger gene, RU49 which is contained by the independent origin cloning vector. In one preferred embodiment the independent origin based cloning vector has undergone homologous recombination with a temperature sensitive shuttle vector in a RecA-host cell, wherein the temperature sensitive shuttle vector encodes a RecA-like protein. In another embodiment the independent origin based cloning vector is a BBPAC, and more preferably a BAC. In a specific embodiment of this type the independent origin based cloning vector has undergone homologous recombination with a temperature sensitive shuttle vector that is pSV1.RecA having the ATCC no. 97968.

The present invention also provides methods of using the modified independent origin based cloning vectors of the present invention to make transgenic animals, perform gene targeting, or perform gene therapy. The independent origin based cloning vectors or linearized nucleic acid inserts derived from the IOBCVs, for example, can be introduced into a eukaryotic cell or animal.

In one such embodiment the eukaryotic cell is a fertilized zygote. In another embodiment the eukaryotic cell is a mouse ES cell. The gene targeting can be performed to modify a particular gene, or to totally disrupt the gene to form a knockout animal.

In this aspect of the present invention, the independent origin based cloning vector contains a nucleic acid that has undergone homologous recombination with a conditional replication shuttle vector in a RecA$^-$ whole cell, in which the conditional replication shuttle vector includes a RecA like protein. In a preferred embodiment the independent origin based cloning vector is a BBPAC. In a more preferred embodiment, the BBPAC has undergone homologous recombination with a TSSV. In the most preferred embodiment, the BBPAC has undergone homologous recombination with the TSSV that is pSV1.RecA having the ATCC no. 97968.

One particular embodiment is a method of using the BBPAC to introduce the nucleic acid into an animal to make a transgenic animal comprising pronuclear injecting of the BBPAC (or a linearized nucleic acid insert derived from the BBPAC) into a fertilized zygote. In one embodiment the animal is a mammal. In a more preferred embodiment the mammal is a mouse. In a specific embodiment of this type the independent origin based cloning vector is a BBPAC and the fertilized zygote is a C57BL/6 mouse zygote. In a preferred embodiment of this type two picoliters (pl) of less than one µg/ml BBPAC DNA is injected. In a more preferred embodiment 2 pl of 0.6 µg/ml of DNA is injected.

The present invention also includes a method of using the BBPAC of the invention to perform gene targeting in a vertebrate cells comprising introducing the BBPAC into the vertebrate cell wherein the nucleic acid that has undergone homologous recombination with the conditional shuttle vector, undergoes homologous recombination with the endogenous chromosomal DNA of the vertebrate cell. In preferred embodiments of this type the vertebrate cell is a mammalian cell. In a more preferred embodiment of this type the mammalian cell is a human cell. In a related embodiment the vertebrate cell is a fertilized zygote and the nucleic acid contains a disrupted gene. In a preferred embodiment the conditional shuttle vector is a TSSV. In a more preferred embodiment the TSSV is pSV1.RecA having the ATCC no. 97968.

The present invention also contains kits for performing homologous recombination on selected nucleotide sequences contained on an independent origin based cloning vector, such as a BBPAC. In one particular embodiment, the kit comprises a conditional replication shuttle vector and a building vector. In a preferred embodiment of this type, the kit further contains a restriction map for the shuttle vector and/or a restriction map for one or more of the building vectors. In a more preferred embodiment, the kit further includes a protocol for using the contents of the kit to perform homologous recombination.

A particular embodiment of the kit contains a TSSV, such as pSV1.RecA and a building vector. In one such embodiment the building vector is pBV.IRES.LacZ.PA. In another such embodiment the building vector is pBV.EGFP1. In yet another such embodiment the building vector is pBV.IRES.EGFP1. In still another such embodiment the building vector is pBV.pGK.Neo.PA.

In a preferred embodiment two or more building vectors are included in the kit. In a more preferred embodiment all four of the above-listed building vectors are included in the kit. Restriction maps for one or more of the building vectors or the TSSV may also be included in the kits. In addition, the kits may also include a protocol for using the contents of the kit to perform homologous recombination. In one specific embodiment, a kit contains pSV1.RecA and one or more of the above-listed vectors also contains fusaric acid and/or chloro-tetracycline.

Accordingly, it is a principal object of the present invention to provide a method for readily and specifically modifying an independent origin based cloning vector in a recombination deficient host cell.

It is a further object of the present invention to provide a method of transiently expressing a RecA-like protein in a RecA$^-$ host cell to allow the specific modification of a gene of interest contained by an independent origin based cloning vector.

It is a further object of the present invention to provide a method of generating deletions, substitutions, and/or point mutations in a specific gene contained by the independent origin based cloning vector in a RecA$^-$ cell.

It is a further object of the present invention to provide a conditional replication shuttle vector which encodes a RecA-like protein, and which further contains a specific nucleic acid in a recombination cassette that selectively undergoes homologous recombination with an independent origin based cloning vector when both vectors are present in a recombination deficient host cell.

It is a further object of the present invention to provide a temperature dependent shuttle vector which encodes a RecA-like protein.

It is a further object of the present invention to provide a temperature dependent shuttle vector which encodes a RecA-like protein, which further contains a specific nucleic acid in a recombination cassette that can selectively undergo homologous recombination with a gene of interest contained by an independent origin based cloning vector, when both vectors are placed in a recombination deficient host cell.

It is a further object of the present invention to provide a temperature sensitive shuttle vector that is pSV1.RecA having the ATCC no. 97968.

It is a further object of the present invention to provide a modified independent origin based cloning vector that can be used for the pronuclear injection of a nucleic acid contained by IOBCV into an animal zygote.

It is a further object of the present invention to provide a modified independent origin based cloning vector that can be transfected into an embryonic stem cell.

It is a further object of the present invention to provide a method of introducing a linearized nucleic acid insert from a modified independent origin based cloning vector into a fertilized zygote of an animal.

It is a further object of the present invention to provide a method of introducing a modified independent origin based cloning vector into an embryonic stem cell.

It is a further object of the present invention to provide a method of purifying a large linearized BBPAC.

These and other aspects of the present invention will be better appreciated by reference to the following drawings and Detailed Description.

BRIEF DESCRIPTION OF THE DRAWINGS

FIG. 1 shows the strategy for targeted BAC modification. (I) Two cloning steps are involved in constructing the shuttle vector. The recombination cassette (genomic fragments A and B; and IRES-LacZP-Poly A marker gene) is first constructed in the building vector and then subcloned into the temperature sensitive pSV1.RecA shuttle vector. (II) Co-integrateformation: Co-integrates can be formed through homologous recombination at either the homology A or the homology B site, with only the former case illustrated. (III) Resolution: Resolved BACs are selected by growth on plates containing fusaric acid and chloramphenicol. Correctly resolved clones are identified by colony hybridizations with an insert specific probe (e.g., a PGK polyA probe).

FIG. 2A depicts a restriction map of the BAC169. The position of several exons are shown. The region of homology A1 (1 kb PCR fragment) and homology B1 (1.6 kb Xba-Hind fragment) are indicated. Abbreviations: XhoI (Xh), EcoRI (R), HindIII (H), XbaI (X), NotI (Not) and PmeI (Pme). FIG. 2B depicts a map of the modified BAC169 with IRES LacZ PolyA insertion (BAC169. ILPA). An extra PmeI site is inserted with the marker gene (asterisk). The size of the two Pme-Not fragments and the PmeI fragment are indicated. Since the marker gene (4 kb) is less than the deleted genomic region (7 kb), the total size of the modified BAC (128 kb) is smaller than the original BAC (131 kb).

FIG. 3A shows a schematic representation of expected Southern blot fragments in BAC169, in co-integrates through homology B1, and in correctly resolved BACs. When analyzing recombination through homology B1, an EcoRI digest is used and homology B1 is used as the probe; when analyzing the recombination through homology A1, a HindIII digest is used and the homology A1 is used as probe.

FIG. 3B shows homology B1 co-integrates. The EcoRI digest of BAC clones and controls are probed with homology B1. 1–4 represent four clones. BAC 169 and pSV1 with the recombination cassette were used as controls.

FIG. 3C shows the analyses of the 5' ends of the resolved BACs. Resolved BAC clones (1–8) were digested with HindIII and probed with homology A1. The controls are homology B1 co-integrates (CI), BAC 169 and the shuttle vector with recombination cassettes.

FIG. 3D shows the analyses of the 3' ends of the resolved BACs. The same procedure is used as described above except the resolved BAC clones were digested with EcoRI and probed with homology B1.

FIG. 4A shows the use of the BAC169 probe which revealed all the restriction fragments.

FIG. 4B shows the use of the pgkpoly A probe which only hybridized to the ILPA insert fragment.

FIG. 4C shows the use of the A2 probe which hybridized to a fragment outside the region of modification. The position of the markers are indicated.

FIG. 5A depicts purified linearized BAC L1 128 kb Not I insert for pronuclear injection. The pulsed field gel is probed with pgkpolyA probe. The numbers represent different fractions. The smear below the intact fragment represent degradation and undigested DNA.

FIG. 5B shows Southern blot analyses of the founder transgenic mice with the lacZ probe. The tail DNA were digested with Bam HI and Southern blot analysis was performed. The negative control consisted of littermates of Y3, Y7 and Y9 mice. The positive control was a conventional transgenic mouse with the lacZ transgene.

FIGS. 5C and 5D show the results of using PCR to determine the presence of BAC ends in the transgenic mice. The DNA at each end corresponding to the vector sequence is amplified and probed with a third oligonucleotide in the middle of the fragment. The appropriate size fragment is indicated. The negative controls are littermates. The positive control was BAC169 DNA.

FIG. 5E shows the germline transmission of the lacZ transgene in the Y7 mouse line. Tail DNA from two litters having eight mice each were prepared and digested with BamHI. Southern blot analysis was performed with the lacZ probe.

FIG. 6C shows the low magnification and FIG. 6D shows the high magnification of the rectangle area indicated in FIG. 6C. Expression in the cerebellum, the detate gyrus and the lineage of the olfactory bulb are indicated (i.e. SVZ, RMS and the OB). Abbreviation Ce, cerebellum; SC, superior collicoli; IC, inferior colliculi; DG, dentate gyrus; VZ, ventricular zone; SVZ, subventricular zone; LV, lateral ventricle; RMS, rostral migratory tract; OB, olfactory bulb; Co, cortex.

FIGS. 7A–C are schematic diagrams containing a hypothetical map of a gene of interest within a selected BAC; the first targeted modification to introduce the positive selection marker gene; and the second modification to delete the promoter of the gene and to generate the short arm.

Figure 9:
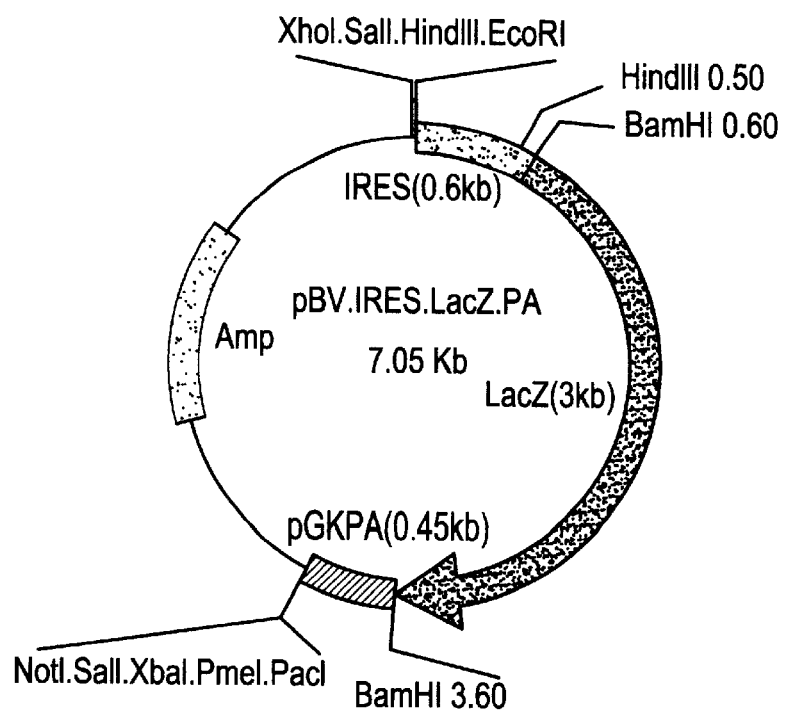

FIG. 9 is the restriction map of pBV.IRES.LacZ.PA. This vector was modified from the pWH10 vector originally constructed by Kim et al. [*MCB*, 12:3636–3643 (1992)].

Figure 10:
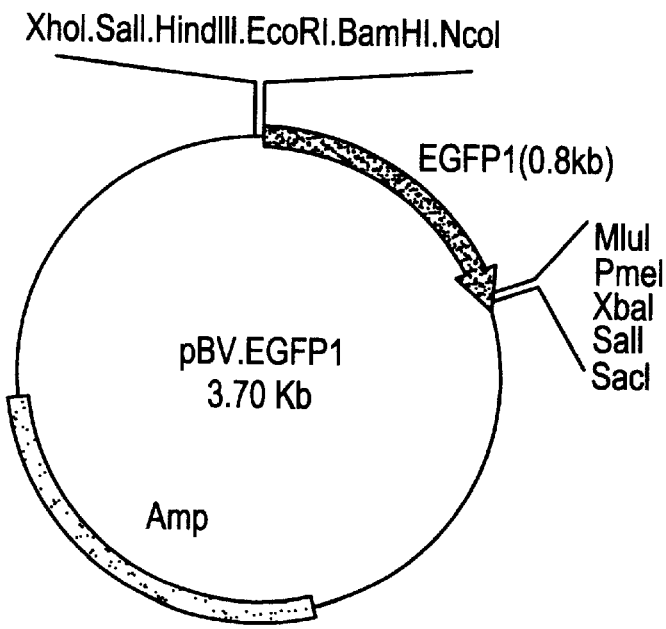

FIG. 10 is the restriction map of pBV.EGFP1. The plasmid is based on pBluescript.KS(+). EGFP1 was from Clonetech.

Figure 11:
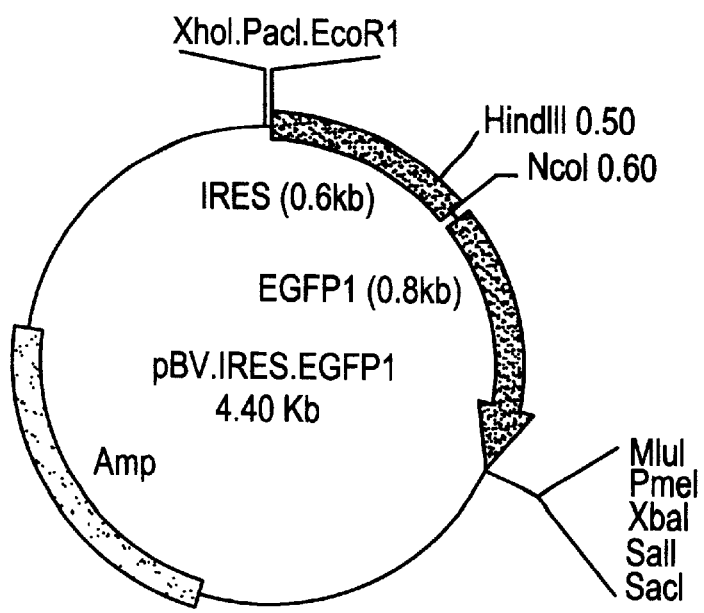

FIG. 11 is the restriction map of pBV.IRES.EGFP1. The plasmid is based on the pBluescript.KS back bone. EGFP1 was from Clonetech.

Figure 12:
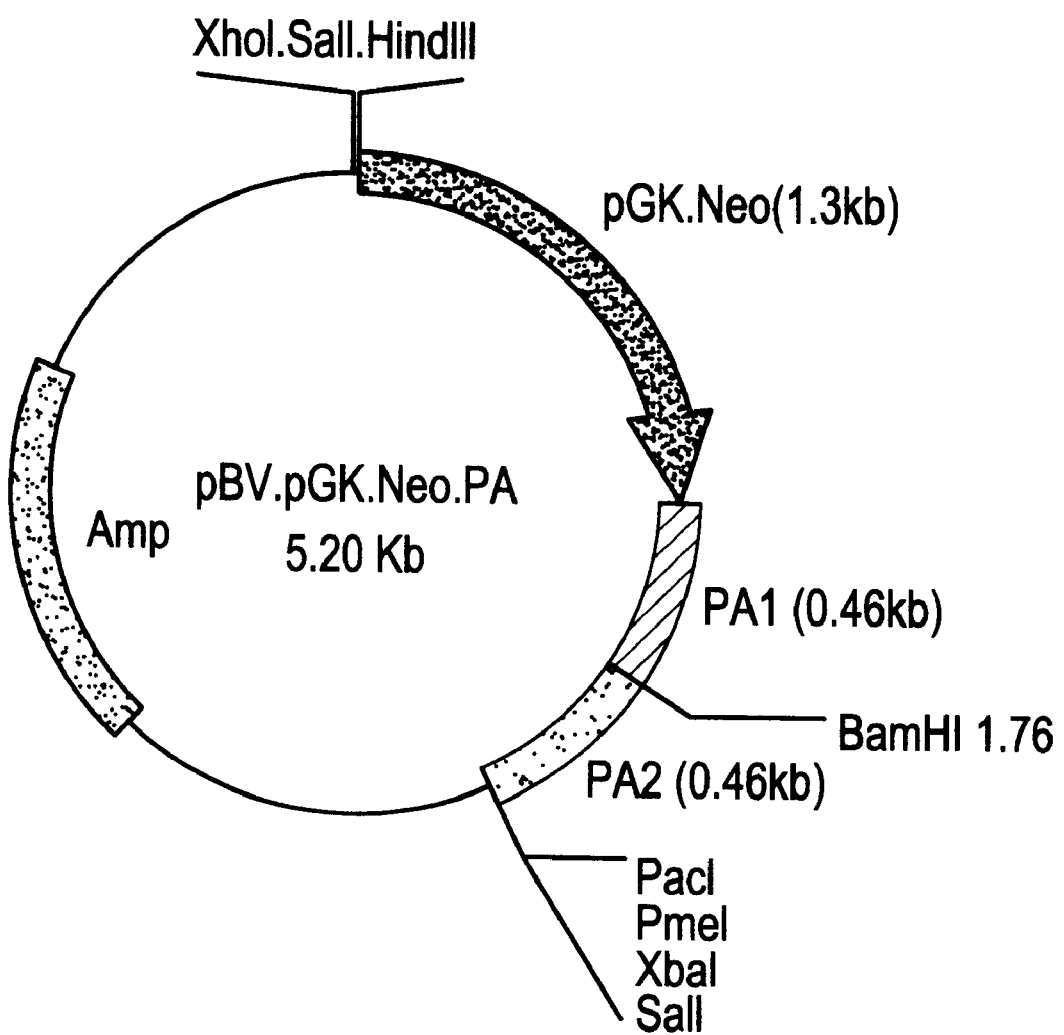

FIG. 12 is the restriction map of pBV.PGK.Neo.PA. The vector is based on a pBS.KS backbone. The pGK.Neo.PA sequences was excised from a pKS.NT vector by digestion with HindIII and BamHI and subcloned into the HindIII/Bam fragment of the BV.IRES.LacA.PA.

DETAILED DESCRIPTION OF THE INVENTION

The present invention provides a simple method for directly modifying an independent origin based cloning vector (IOBCV) in recombination deficient host cells including generating deletions, substitutions, and/or point mutations in a specific gene contained in the independent origin based cloning vector. Such modifications may be performed with great specificity. The modified independent origin based cloning vectors of the present invention can be used to introduce a modified heterologous gene into a host cell. One specific use of such a modified vector is for the production of a germline transmitted independent origin based cloning vector transgenic animal.

Targeted independent origin based cloning vector modification can be used for functional studies in diverse biological systems. The ability to efficiently modify a independent origin based cloning vector and generate an IOBCV-transgenic animal has important applications for functional analyses of genes in vivo. First, modified independent origin based cloning vectors can be used to study regulation of genes or gene complexes in transgenic animals such as mice. Since modified independent origin based cloning vectors can be used to study gene function in vivo, a deletion, substitution and point mutation within a given gene can be made in a independent origin based cloning vector, and the independent origin based cloning vector containing the modified gene can be reintroduced in vivo in its endogenous expression pattern. Furthermore, targeted independent origin based cloning vector modification can be used to create targeted expression of a selected gene, in the expression pattern of another gene, without prior knowledge of all of the regulatory elements of the selected gene. An important application of this type is targeted expression of the cre recominase for tissue/cell type specific gene targeting [Kuhn et al., *Science* 269:1427 (1995); Tsien et al., *Cell* 87:1317 (1996)]. Finally, modified independent origin based cloning vectors can be used to generate large DNA constructs particularly for gene targeting in ES cells and in vivo.

In one specific embodiment of the present invention the independent origin based cloning vector is a Bacterial Artificial Chromosome (BAC) modified in a host *E. coli* cell. A targeted BAC modification system has several advantages over a conventional yeast based modification system. First, a modified BAC automatically returns to the recombination deficient state after modification, ensuring stable maintenance of the modified BAC in the host strain. Second, BAC DNA can be very easily purified in relatively large quantities and high quality, allowing for use in biological experimentation including pronuclear injection. Third, since it is much easier to construct a BAC library than a YAC library, there are many more BAC libraries available from different species of animal, plants and microbes [Woo et al., *Nucleic Acids Res.*, 22:4922 (1994); Wang et al., *Genomics* 24:527 (1994); Wooster et al., *Nature* 378:789 (1995)]. Most BACs also include all the necessary regulatory elements (i.e. LCRs and enhancers) to obtain dose dependent and integration site independent transgene expression [Dillon et al. *Trends Genet.* 9:134 (1993); Wilson et al., *Annu. Rev. Cell. Biol.* 6:679 (1990); Bradley et al., *Nature Genet.* 14:121 (1997)]. Targeted BAC modification can be applied successively to dissect these elements. In addition, such a modified BAC may be used to generate a transgenic animal. The BAC (or PAC) stably integrates into the animal cell genome. The transgenic animal can be used for functional studies, or for generating a desired gene product, such as producing a human protein in the milk of a transgenic mammal [Drohan et al. U.S. Pat. No. 5,589,604, Issued Dec. 31, 1996]. Alternatively such modified BACs or PACs may be used for delivering a specific gene in gene therapy. In the Example below, a modified BAC has been successfully inserted into a murine subject animal, and in vivo heterologous gene expression has been demonstrated.

The methodology of the present invention is very general. Whereas the targeted independent origin based cloning vector modification is demonstrated on BACs, the system is readily applicable to BBPACs in general including PACs, P1 and other vectors propagated in the recombination deficient *E. coli*. In addition, the BAC modification exemplified herein, is also apropo to Mammalian Artificial Chromosomes. For example, Harrington et al. [*Nature Genetics*, 15:345–355 (1997)] have used BAC derived DNA as a component of their Human Artificial Chromosome. Therefore, the use of such human artificial chromosomes can include the BAC modification taught by the present invention.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning. A Laboratory Manual*, Second Edition (1989) Cold Spring Harbor aboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

As used herein an "IOBCV" is an independent origin based cloning vector. One example of such a cloning vector is a BBPAC defined below. An IOBCV generally comprises a nucleic acid insert which either is or contains a gene of interest.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in viva, i.e., capable of replication under its own control.

As used herein, a "Bacterial or Bacteriophage-Derived Artificial Chromosome" or "BBPAC" denotes a vector that is derived from a bacterium or bacteriophage such as a Bacterial Artificial Chromosome (BAC) which is an *E. coli* F element based cloning system, a P1-Derived Artificial Chromosome (PAC) or a lambda-based cosmid. In one embodiment, the BBPAC encodes up to 500 kilobases of genomic sequences. In a preferred embodiment, the BBPAC encodes between 120 to 180 kilobases of genomic sequences. In one particular embodiment the BBPAC encodes 130 kilobases of genomic sequences. A BBPAC used for gene targeting can be referred to as a "BBPAC targeting construct" and contains a nucleic acid insert comprising the gene targeting construct.

A "gene targeting construct" as used herein is used interchangeably with "targeting construct" and is a nucleic acid that when introduced into a cell undergoes homologous recombination with the endogenous chromosomal DNA of the cell. The nucleic acid is introduced into the cell to induce a modification of a particular gene contained on the endogenous chromosomal DNA, including in particular cases, to disrupt that gene to create a knockout animal.

As used herein a recombinant deficient host cell is "RecA$^-$" when the host cell is unable to express a RecA-like protein, including recA itself, which can support homologous recombination. In the simplest case, the gene encoding the RecA-like protein has been deleted in a RecA$^-$ host cell. Alternatively the RecA-host cell contains a mutation in the recA gene that impairs its function.

A "RecA-like protein" is defined herein to have the meaning generally accepted in the art except as used herein the recA protein itself is included as being a specific RecA-like protein. RecA-like proteins are proteins involved in homologous recombination and are homologs to recA [Clark et al., *Critical Reviews in Microbiology* 20:125–142 (1994)]. The recA protein is the central enzyme in prokaryotic homologous recombination. It catalyzes pairing and strand exchange between homologous DNA molecules, and functions in both DNA repair and genetic recombination [McKee et al., *Chromosoma* 7:479–488 (1996)]. A number of RecA-like proteins have been found in eukaryotic organisms and yeast [Reiss et al., *Proc. Natl. Acad. Sci.* 93:3094–3098 (1996)]. Two RecA-like proteins in yeast are Rad51 and Dmc1 [McKee et al. (1996) supra]. Rad51 is a highly conserved RecA-like protein in eukaryotes [Peakman et al., *Proc. Natl. Acad. Sci.* 93:10222–10227 (1996)].

As used herein a "gene of interest" is a gene contained by a host cell genome or more preferably an independent origin based cloning vector that has been selected to undergo homologous recombination with a specific nucleic acid contained in a recombination cassette. A gene of interest can be either specifically placed into the host cell or independent origin based cloning vector for this purpose, or already contained by the host cell or independent origin based cloning vector .

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation. The present invention provides a recombination cassette that includes two homology fragments interrupted by an insertion, deletion or mutation sequence.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

"Homologous recombination" refers to the insertion of a modified or foreign DNA sequence contained by a first vector into another DNA sequence contained in second vector, or a chromosome of a cell. The first vector targets a specific chromosomal site for homologous recombination. For specific homologous recombination, the first vector will contain sufficiently long regions of homology to sequences of the second vector or chromosome to allow complementary binding and incorporation of DNA from the first vector into the DNA of the second vector, or the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended or expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

A particular nucleotide sequence comprising a gene of interest, whether genomic DNA or cDNA, can be isolated from any source, particularly from a human cDNA or genomic library. In view and in conjunction with the present teachings, methods well known in the art, as described above can be used for obtaining such genes from any source (see, e.g., Sambrook et al., 1989, supra).

Accordingly, any animal cell potentially can serve as the nucleic acid source for the molecular cloning of any selected gene. The DNA may be obtained by standard procedures known in the art from cloned DNA (e.g., a DNA "library"), and preferably is obtained from a cDNA library prepared from tissues with high level expression of the protein by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. 1, 11). Clones derived from genomic DNA may contain regulatory and intron DNA regions in addition to coding regions; clones derived from cDNA will not contain intron sequences.

The present invention provides methods for selectively performing homologous recombination in a cell that normally cannot independently support homologous recombination. A specific nucleic acid is inserted into a recombination cassette that selectively integrates into a particular nucleotide sequence when the recombination deficient cell is transiently induced to support homologous recombination. More particularly, the present invention allows the integration of a specific nucleic acid into a particular nucleotide sequence of a gene of interest. The methods provided by the present invention minimize the nonspecific nucleotide sequence rearrangements and deletions, which are characteristic of other systems which involve host cells that normally support homologous recombination.

In one case the specific nucleic acid can encode an entirely different protein than the gene of interest, and the gene of interest may be selected for the tissue specificity of its promoter, for example for use in generating a transgenic animal, or in a gene therapy protocol. In one such embodiment the rat preproenkephalin gene may be used as the gene of interest since the preproenkephalin promoter has been shown to confer brain expression and synaptic regulation in transgenic mice. [Donovan et al., Proc. Natl. Acad. Sci. 89:2345–2349 (1992)]. In the Example below, the murine zinc finger gene, RU49 was used as the gene of interest. Alternatively, the specific nucleic acid can be constructed so as to cause a deliberate and specific modification in the sequence of the gene of interest, for example for inducing a change in the amino acid sequence of the gene product, such as is typically done in site-directed mutagenesis protocols.

In one aspect of the present invention, the recombination deficient host cell cannot independently support homologous recombination because the host cell is RecA⁻. However, as any person skilled in the art would readily understand, alternative causes for recombination deficiency may be rectified by methods that are analogous to those taught by the present invention and/or readily apparent in view of such teachings. For example recombination deficiency may be due to a deficiency of an alternative recombination protein such as another Rec protein including recB, recC, recD, and recE [Clark et al., *Critical Reviews in Microbiol.* 20:125–142 (1994)] which may be manipulated in a manner that is analogous to that taught herein for RecA-like proteins.

In the case of a RecA- host cell, inducing the host cell to transiently support homologous recombination comprises inducing the transient expression of a RecA-like protein in the host cell. Such induction may be performed by expressing a RecA-like protein contained by the recombination deficient host that is under the control of an inducible promoter.

In a preferred aspect of the invention inducing the transient expression of the RecA-like protein is performed with a conditional replication shuttle vector that encodes the RecA-like protein. Conditional replication shuttle vectors can also include pBR322 in a polyA temperature-sensitive bacterial strain. Preferably the conditional replication shuttle vector is a temperature sensitive shuttle vector (TSSV) that replicates at a permissive temperature, but does not replicate at a non-permissive temperature.

Inducing the transient expression of the RecA-like protein consists of transforming the host cell with the TSSV at a permissive temperature, and growing the host cell at a non-permissive temperature. The TSSV encodes a RecA-like protein that is expressed in the host cell and supports the homologous recombination between a specific nucleic acid contained in a recombination cassette and the particular nucleotide sequence contained in the host cell. The TSSV encoding the RecA-like protein is diluted out when the host cell is grown at the non-permissive temperature.

In a more intricate version of the present invention, the particular nucleotide sequence which has been selected to undergo homologous recombination is contained by an independent origin based cloning vector (IOBCV) that is comprised by the host cell, and neither the independent origin based cloning vector alone, nor the independent origin based cloning vector in combination with the host cell, can independently support homologous recombination. In a particular embodiment of this type both the independent origin based cloning vector and the host cell are RecA⁻, and inducing the host cell to transiently support homologous recombination comprises inducing the transient expression of the RecA-like protein to support homologous recombination in the host cell. The independent origin based cloning vector can be a BBPAC, such as the BAC exemplified below and the host cell can be a host bacterium, such as *E. coli*.

The independent origin based cloning vectors for use in the methods of the present invention can be obtained from a number of sources. For example, *E. coli*-based artificial chromosomes for human libraries have been described [Shizuya et al., Proc. Natl. Acad. Sci. 89:8794–8797 (1992); Ioannou et al., In *Current Protocols in Human Genetics* (ed. Dracopoli et al.) 5.15.1–5.15.24 John Wiley & Sons, New York (1996); Kim et al., Genomics 34:213–218 (1996)]. Libraries of PACs and BACs have been constructed [reviewed in Monaco et al., *Trends Biotechol.*, 12:280–286 (1994)], that are readily isolated from the host genomic background for example by classical alkaline lysis plasmid preparation protocols [Birnboim et al., *Nucleic Acids Res.* 7:1513–1523 (1979)], or alternatively, with the use of a nucleobond kit, a boiling Prep, or by cessium gradient (Maniatis, supra). BAC, PAC, and P1 libraries are also available for a variety of species (e.g. Research Genetics, Inc., Genome Research, Inc., Texas A&M has a BAC center to make a BAC library for livestock and important crops). Also BACs can be used as a component of mammalian artificial chromosomes.

An independent origin based cloning vector that is a BAC can be isolated using a cDNA or genomic DNA probe to screen a BAC genomic DNA library, for example. The use of a mouse genomic BAC library from Research Genetics is exemplified below. A positive BAC can generally be obtained in a few days. To insert a gene of interest into a selected locus in the BAC, the region of insertion can be mapped for restriction enzyme sites. Whereas subcloning is necessary for detailed mapping, it is generally unnecessary since rough mapping is usually sufficient. As is readily apparent, other independent origin based cloning vector genomic libraries can be screened and the isolated independent origin based cloning vectors manipulated in an analogous fashion.

The conditional replication shuttle vectors of the present invention are constructed so as to contain a recombination cassette that can selectively integrate into the nucleotide sequence of the gene of interest encoded by the independent origin based cloning vector. Such conditional replication shuttle vectors can be constructed by inserting a PCR amplified RecA-like gene into an appropriate conditional replication shuttle vector which either contains a specific drug resistant gene or can be subsequently modified to contain one. In a preferred embodiment the drug resistant gene can also be counter-selected against, such as with, tetracycline and fusaric acid. Alternatively, in addition to the drug resistant gene the conditional shuttle vector can also contain a counter-selection gene such as a gene that confers sensitivity to galactose, for example.

In the Example below, the *E. coli* K12 recA gene (1.3 kb) is inserted into the BamHI site of a pMBO96 vector. In this case the vector already carried a gene that bestows tetracycline resistance, and in addition contains a pSC101 temperature sensitive origin of replication, which allows the plasmid to replicate at 30 degrees but not at 43 degrees celsius.

The RecA-like protein of a conditional replication shuttle vector can be controlled by either an inducible promoter or a constitutive promoter. In one particular embodiment the transient expression of the RecA-like protein is achieved by the transient induction of the inducible promoter in a host cell. In another embodiment, the constitutive promoter is the endogenous *E. coli* recA promoter.

The conditional replication shuttle vector should also contain at least one unique cloning site. When a building vector is used for the construction of the recombination cassette as described below, one unique site is reserved for transferring the recombination cassette containing the specific nucleic acid from the building vector to the conditional replication shuttle vector. For example a polylinker can be inserted between two specific restriction sites to create additional restriction sites that allow cloning of the recombination cassette into the conditional replication shuttle vector. In any case the conditional replication shuttle vector created should minimally contain a recombination cassette comprising the specific nucleic acid, (e.g., containing a point mutation, deletion or a marker gene) flanked at both the 5' and 3' ends by genomic fragments containing 400 basepairs or more of the gene of interest of the independent origin based cloning vector.

In certain cases a building vector is used to construct the recombination cassette. Two small genomic fragments, each containing about 500 basepairs (400 basepairs to 600 basepairs is sufficient) of the gene of interest are cloned into the building vector (e.g., pBV1) in appropriate order and orientation to generate the flanking regions of the recombination cassette. DNA containing a promoter sequence 5' to the specific nucleic acid, which in turn is 5' to a polyadenine addition signal sequence, is inserted between the two genomic fragments in the proper orientation. The recombination cassette is then transferred into the conditional replication shuttle vector (e.g., pSV1.RecA). The recombination cassette, the RecA-like protein gene, and the drug resistant gene are linked together on the conditional replication shuttle vector such that when the specific nucleic acid integrates into the particular nucleotide sequence, the RecA-like protein gene and the drug resistant gene remain linked together, and neither the RecA-like protein gene nor the drug resistant gene remain linked to the integrated specific nucleic acid. In a preferred embodiment the conditional replication shuttle vector is a TSSV and the TSSV is pSV1.RecA having the ATCC no. 97968, which has been deposited with the American Type Culture Collection, 10801 University Boulevard, Manassas, Va., 20110-2209, on Mar. 25, 1997 under the Budapest Treaty.

According to the methods of the present invention the conditional replication shuttle vector is transformed into a RecA⁻ host cell containing the independent origin based cloning vector. The independent origin based cloning vector can also contain a gene which bestows resistance to a host cell against a corresponding toxic agent/drug such as an antibiotic or in a specific embodiment, chloramphenicol. The cells are grown under the conditions in which the conditional replication shuttle vector can replicate (e.g., when the conditional replication shuttle vector is a TSSV which replicates at 30° but not at 43°, the host cell is grown at 30° C.) and the transformants can be selected via the specific drug resistant gene (or first drug resistant gene) carried by conditional replication shuttle vector, and the second drug resistant gene carried by the independent origin based cloning vector. Since the conditional replication shuttle vector also carries the RecA-like protein gene, homologous recombination can occur between the conditional replication shuttle vector and the independent origin based cloning vector to form co-integrates through the sequence homology at either the 5' or the 3' flanking regions of the recombination cassette. The co-integrates then can be selected by growing the cells on plates containing the first and second drugs at non-permissive conditions (e.g. for the TSSV above, at 43° C.) so that the non-integrated, free conditional replication shuttle vectors are lost. This results in the selection for host cells carrying the integrated conditional replication shuttle vectors, (which co-integrate either into the independent origin based cloning vector or into the host chromosome). Correct independent origin based cloning vector co-integrates can be identified by PCR or more preferably with Southern blot analyses.

The co-integrates can then be re-streaked onto plates containing the second drug, (i.e., the drug which the gene initially carried by the independent origin based cloning vector protects against) and grown under non-permissive conditions overnight. A fraction of the co-integrates undergo a second recombination event (defined as resolution), through sequence homology at either the 5' or the 3' flanking regions of the recombination cassette. The resolved independent origin based cloning vector automatically loses both the first drug resistant gene (i.e., the specific drug resistant gene contained by the conditional replication shuttle vector) and the RecA-like protein gene due to the linkage arrangement of the RecA-like protein gene, the drug resistant gene and the specific nucleic acid on the conditional replication shuttle vector, described above. In addition, the excised conditional replication shuttle vector cannot replicate under the non-permissive conditions and is therefore diluted out.

The resolved independent origin based cloning vectors can be further selected for by growing the host cells (e.g., at 37° C.) on plates containing the second drug and an agent that counterselects against cells containing the gene resistant to the first drug (e.g., a gene conferring tetracycline resistance may be counter-selected against with fusaric acid). The resolved independent origin based cloning vector will be either the original independent origin based cloning vector or the precisely modified independent origin based cloning vector. One method to identify the correctly resolved BAC is to choose 5–10 colonies and prepare a miniprep DNA. The DNA can then be analyzed using Southern blots to detect the correct targeting events. Alternatively, the desired clones can be identified by colony hybridization using a labeled probe for the specific nucleic acid contained by the recombination cassette. Such probes are well known in the art, and include labeled nucleotides probes that hybridize to the nucleic acid sequence. Alternatively, a marker nucleic acid can be included in the recombination cassette and constructed so as to remain with the specific nucleic acid upon integration into the independent origin based cloning vector.

The marker nucleic acid can encode a protein that confers a specific drug resistance to the host cell, a protein that confers a particular physical characteristic to the cells, such as a green fluorescent protein, or it can be any other marker protein including e.g., β-galactosidase.

The methods of homologous recombination of the present invention are selective, and nonspecific nucleotide sequence rearrangements either do not occur, or are essentially undetectable by one or more conventional methods of analysis. One such method includes pulsed field gel mapping of the modified independent origin based cloning vector and the unmodified independent origin based cloning vector to determine whether any unexpected deletions, or insertions or rearrangement were generated during the modification procedure. In one particular embodiment, the same filter can be probed separately with a probe for the whole independent origin based cloning vector, with a probe for the specific nucleic acid, and a probe for a region of the gene of interest that has not been modified. A restriction enzyme digestion can reveal a finger print of the modified independent origin based cloning vectors indicating whether the fragments are preserved. Such a restriction enzyme digestion is exemplified below. Restriction enzyme digestions can be repeated with one or more additional restriction enzymes selected with respect to the restriction site map of the independent origin based cloning vector.

In an alternative method, the modified independent origin based cloning vector and the unmodified independent origin based cloning vector can be assayed with both a probe specific for any region of the DNA contained by the recombination cassette predicted to be inserted into the independent origin based cloning vector (e.g., the promoter sequence, the specific nucleic acid, and a polyadenine addition signal sequence) and a probe specific for a region outside of the modification region (e.g., near the promoter region but outside of the modification region).

A modified independent origin based cloning vector of the present invention can be purified by gel filtration, e.g. a column filled with SEPHAROSE CL-4B yielded intact linear BAC DNA. The column can be pre-equilibrated in an appropriate buffer, as described in the Example below. The purified DNA can be directly visualized with ultraviolet light after ethidium bromide staining, for example. Columns such as the SEPHAROSE CL-4B column also can efficiently separate degraded DNA from the pure linear DNA.

The present invention also provides methods of using the modified independent origin based cloning vectors of the present invention. Such modified independent origin based cloning vectors contain a nucleic acid that can be inserted into an animal to make a transgenic animal. The modified independent origin based cloning vectors of the present invention can be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, *J. Biol. Chem.* 267:963–967; Wu and Wu, 1988, *J. Biol. Chem.* 263:14621–14624; Hartmut et al., Canadian Patent Application No. 2,012,311, filed Mar. 15, 1990).

Constitutive expression of any selected gene, even if at low levels is contemplated by the present invention. Various therapeutic heterologous genes can be inserted into an independent origin based cloning vector of the invention such as but not limited to adenosine deaminase (ADA) to treat severe combined immunodeficiency (SCID); marker genes or lymphokine genes into tumor infiltrating (TIL) T cells [Kasis et al., *Proc. Natl. Acad. Sci. U.S.A.* 87:473 (1990); Culver et al., ibid. 88:3155 (1991)]; genes for clotting factors such as Factor VIII and Factor IX for treating hemophilia [Dwarki et al. *Proc. Natl. Acad. Sci. USA*, 92:1023–1027 (19950); Thompson, *Thromb. and Haemostatis*, 66:119–122 (1991)]; and various other well known therapeutic genes such as, but not limited to, β-globin, dystrophin, insulin, erythropoietin, growth hormone, glucocerebrosidase, β-glucuronidase, α-antitrypsin, phenylalanine hydroxylase, tyrosine hydroxylase, ornithine transcarbamylase, apolipoproteins, and the like. In general, see U.S. Pat. No. 5,399,346 to Anderson et al.

One particular method comprises the pronuclear injection of the modified independent origin based cloning vector into a fertilized animal zygote. Such a method is exemplified below with the modified independent origin based cloning vector being a BAC which has been linearized, and the animal zygote being a mouse zygote. 2 pl of 0.6 μg/ml of BAC DNA was injected.

The presence of both ends of the modified independent origin based cloning vector can be assayed for in the transgenic animal to determine if the intact nucleic acid insert of the IOBCV has been integrated into the genome. Since both ends of the nucleic acid insert contain some vector sequence, PCR primers specific to the vector sequence can be generated and used to amplify the transgenic DNA. The amplified products can then be probed with a third labeled oligonucleotide probe within the amplified region.

The transgenic animals that are formed give rise to germline transmission after appropriate breeding (B6/CBA mice were used in the Example). The ratio of transgenic animals to wild type animals should follow Mendelian genetics.

The expression of the specific nucleic acid and/or the gene of interest inserted into the transgenic animal can be determined by a variety of methods well known in the art which depend on the nature of the insert. For example, enzymes can be appropriately assayed for activity, in the case of β-galactosidase, whole mount staining can be performed, in situ hybridization can be used to detect the corresponding mRNA, and specific antibodies can be used to identify the expression of a corresponding protein. In preferred embodiments such expression will be evident only in cells in which the endogenous gene of interest is expressed. In the Example, in which the gene of interest was the murine zinc finger RU49, and the specific nucleic acid inserted therein was the lacZ marker gene, analyses of the expression of the lacZ marker gene in the entire cerebellum of postnatal day 6 transgenic mice closely resembled the corresponding endogenous RU49 expression pattern.

The present invention also provides the use of targeted BBPAC modification to obtain a high rate of gene targeting in vertebrates. The BBPAC contains a nucleic acid insert comprising the gene targeting construct. The circular BBPAC can be used, or preferably the linearized nucleic acid insert is used. In either case, the BBPAC or linearized nucleic acid insert can be purified by gel filtration as described herein.

In one aspect of the invention the gene targeting is performed in ES cells using a BBPAC gene targeting construct that is greater than 100 kb. In a general sense, the BBPAC gene targeting construct is similar to the conventional positive selection gene targeting construct (FIG. 7): it contains two regions of homology, a long arm (>80 kb) and a short arm (10–20 kb), with the neo cassette (pgk-neo-polyA) introduced into the middle of the BBPAC. Two targeted BBPAC modifications are used to make this construct. The first modification is to introduce the neo gene to disrupt the gene of interest in the BBPAC. A second modification is to create the short arm (10–20 kb). The reason for the second modification is enable the use of an endogenous probe flanking the short arm (KO probe) to detect a polymorphism between the targeted allele and the wild type allele in screening ES cell clones (FIG. 7; *Gene Targeting, a practical approach*, supra).

A preferred version of the BBPAC gene targeting methodology of the present invention also includes negative selection. The conventional negative selection cassettes, such as the use of the herpes thymidine kinase cassette or the diphtheria toxin gene cassette, may not always work with BBPAC constructs since BBPAC DNA tends to exist in transfected mammalian cells as episomal DNA for a long period of time [Baker et al., *NAR* 25:1950–1956]. In one example, the EGFP1 cassette can be used as a negative screening cassette. In this case, in the second step of modification to generate the short arm, the CMV promoter driven green fluorescent protein (EGFP-1) and the polyA signal can be introduced. Unlike other negative selection cassettes, GFP is not toxic to the cells but serves as a fluorescent marker protein. When gene targeting occurs, the EGFP-1 cassette will be lost and the cell will not exhibit a green fluorescence under UV light. On the other hand, when the BBPAC integrates non-homologously, the EGFP-1 cassette also integrates, and the cells will therefore exhibit the green fluorescence under UV. For the definitive Southern blot analyses only those neo resistant cell lines which do not exhibit a green fluorescence under UV light are chosen.

The process of generating the targeted ES cells with a BBPAC targeting construct is essentially the same as with the conventional protocols (Gene Targeting, A Practical Approach, supra), except for the following steps. First the linearized intact BBPAC nucleic acid insert (for example) is purified using the gel filtration procedure described herein. Next, the transfection of ES cells with the linearized intact BBPAC nuclieec acid insert is performed as described by Baker [*NAR*, 25:1950–1956 (1997)], using psoralen-inactivated adenovirus as carriers, for example.

The method enables transfection efficiency in mammalian cells with linear BBPAC DNA to be similar to the transfection efficiency of a conventional DNA construct. On the other hand, the BBPAC targeting construct can potentially provide 10–100 fold higher targeting frequency than the conventional targeting construct, thereby making gene targeting in mouse ES cells easier and cheaper, since only a few dozen colonies need to be isolated and screened to obtain the targeted clones.

The present invention further provides a method of performing gene targeting in fertilized vertebrate zygotes by the injection of a BBPAC targeting construct, or preferably the linearized intact BBPAC nucleic acid insert containing the targeting construct to generate a transgenic knock-out animal (TKO). A large targeting construct (>100 kb) can provide a very high targeting rate (predicted by mathematical modeling described above) and gene targeting can be directly performed with a fertilized vertebrate zygote via pronuclear injection of the modified BBPAC targeting construct. TKO methodology has previously been attempted by Brinster et al. [*PNAS*, 86:7087–91 (1989)] with a small DNA construct (2.6–8.9 kb) but those workers only obtained a relatively low targeting rate (0.2%). The large homology DNA in the BBPAC (>100 kb) of the present invention increases the targeting rate to a favorable range of 2% to 10%.

In one such embodiment, the design of the gene targeting construct is similar to the ES cell targeting construct except that instead of the neo gene, an IRES-GFP cassette or an IRES-lacZ cassette is fused to an exon of the gene of interest to disrupt the gene (FIG. 7). As described above, two consecutive steps of BBPAC modifications are involved in generating the BBPAC containing the gene targeting construct.

The modified BBPAC TKO construct can be prepared in milligram quantities and linearized as described above. The linearized DNA then is introduced into the fertilized zygote by a standard protocol, e.g., pronuclear injection (Hogan et al., (1986) supra). The transgenic animal is then identified by standard Southern blots. The gene targeting event can be further identified by digesting DNA of the transgenic animal with appropriate enzymes, such as enzyme X, (FIG. 7) and probed with the flanking KO probe (FIG. 7). Mice with the targeting event will have an additional band of the appropriate size. Such gene targeting events can further be confirmed by expression of the GFP or LacZ marker gene in the expression pattern of the targeted endogenous gene, since the construct is designed to trap the endogenous promoter.

The TKO method has important ramifications in the field of vertebrate genetics. It enables gene targeting in many organisms that do not have ES cells, such as zebra fish, rats and other mammals. This will help to generate better animal models for human diseases (e.g., rats and monkeys), or to create genetically targeted animals suitable for organ transplants (such as pigs or baboons) or for commercial reasons (e.g., leaner pork or beef). This method also has additional advantages, even for gene targeting in mice. For example, this method will automatically provide germline transmission, since transgenic animals are rarely chimeric. It also enables targeted mice in strains other than the 129 strain to be obtained, and avoids the expensive and time-consuming out-breeding protocols.

In still another aspect of the present invention, methods of performing gene targeting in somatic cells using BBPAC targeting constructs are provided. Since gene targeting in somatic cells is also dependent on the length of homology, using large DNA targeting construct also improves the targeting rate in somatic cells. The experimental design in this case is similar to that with the ES cells described above. Somatic cell gene targeting is useful in gene therapy, for example, in a targeted insertion of a functional gene in a hereditary disease of the hematopoietic system. Such methods are also useful to generate targeted cell lines for experimental purposes.

Conditional replication shuttle vectors that encode a RecA-like protein are also provided by the present invention. The RecA-like protein can be controlled by either an inducible promoter or a constitutive promoter. The conditional replication shuttle vector is preferably a temperature sensitive shuttle vector (TSSV). In one such embodiment the TSSV contains both a gene that confers tetracycline resistance and a RecA-like protein that is recA. In a preferred embodiment, the TSSV is pSV1.RecA having the ATCC no. 97968.

Independent origin based cloning vectors that contain a gene of interest that has been modified by the methods of the present invention are also included in the present invention. More particularly such independent origin based cloning vectors have undergone homologous recombination with a conditional replication shuttle vector in a RecA⁻ host cell, wherein the conditional replication shuttle vector encodes a RecA-like protein. In a preferred embodiment the independent origin based cloning vector has undergone homologous recombination in a RecA⁻ host cell with a temperature sensitive shuttle vector encoding a RecA-like protein. In a preferred embodiment the modified independent origin based cloning vector is a BAC that has undergone homologous recombination with the temperature sensitive shuttle vector pSV1.RecA having the ATCC no. 97968.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE

HOMOLOGOUS RECOMBINATION BASED MODIFICATION IN E. COLI AND GERMLINE TRANSMISSION IN TRANSGENIC MICE OF AN 131 KILOBASE BACTERIAL ARTIFICIAL CHROMOSOME

Introduction

Bacterial based artificial chromosomes, such as Bacterial artificial chromosomes (BACs) and P-1derived artificial chromosomes (PACs), are circular bacterial plasmids that may propogate as large as 300 kb of exogenous genomic DNA (Shizuya et al, PNAS, 89, 8794–97, 1992; Ioannou et al, Nature Genet., 6, 84–90, 1994). For the majority of BAC and PAC libraries, the average size of the insert is 130–150 kb. There are several advantages of using bacterial based artificial chromosomes for genomic and functional studies, compared to the yeast based system (i.e. YACs): First, BAC and PAC libraries are much easier to construct due to higher cloning efficiency. Second, BACs and PACs are propagated in recombination deficient *E. coli* host cells, so they have high stability and minimal chimerism. No rearrangements have been observed in BACs or PACs after 100 generations of growth. Third, isolation of BAC and PAC DNA is very easy since they exist as supercoiled circular plasmids that are resistant to shearing. Conventional bacterial plasmid DNA isolation methods can be applied to obtain milligrams of intact BAC or PAC DNA. Finally, direct DNA sequencing can be applied to BAC or PAC DNA, which is not possible for YAC DNA. These advantages have made BACs and PACs important tools for genome studies in many species.

Although BBPACs are useful for physical mapping in genome studies, no simple method is available to modify BBPACs, as is available for the YACs. A simple homologous recombination based BBPAC modification method is disclosed, termed targeted BBPAC modification (See FIG. 7 for a schematic representation of the method). This method allows precise modification, such as marker insertion, deletion, point mutation, at any chosen site within a given BBPAC. This method involves several steps: isolation of BBPACs using cDNA or genomic DNA probes, simple mapping and partial sequencing of the BBPACs, cloning of the shuttle vector, targeted modifications, pulsed field gel analyses of the modified BBPACs, and finally preparation of linearized BBPAC DNA for functional studies, such as pronuclear injection to produce BBPAC transgenic mice. Since the method is simple and reliable, it is reasonable to expect that the entire procedure, from the step of screening for a BBPAC with a cDNA or genomic DNA probe to the step of modified BBPACs ready for functional studies, can be completed within 6–8 weeks.

Using this method, the IRES-LacZ marker gene has been introduced into an 131 kb bacterial artificial chromosome (BAC) containing the murine zinc finger gene, RU49. No rearrangements or deletions are detected in the modified BACs. Furthermore, transgenic mice are generated by pronuclear injection of the modified BAC and germline transmission of the intact BAC has been obtained. Proper expression of the lacZ transgene in the cerebellum has been observed, which could not be obtained with conventional transgenic constructs. In summary, a novel and efficient method has been developed to modify BACs, PACs and P1 for in vivo studies of gene expression and gene function.

Materials and Methods

1. Isolation and Initial Mapping of BACs (I) BAC isolation (3–4 days):

A BAC clone is isolated with either a unique cDNA or genomic DNA probe. BAC libraries for various species, (in the form of high density BAC colony DNA membrane) are available from Research Genetics, Inc. and Genome Research, Inc. The mouse 129 genomic BAC library from Research Genetics has proved to be a good source for genomic DNAs. To avoid damage to the membrane, the probe is first tested on a mouse genomic Southern blot to ensure that the probe does not contain any repetitive elements. The library is screened according to manufacture's direction. The positive clones can be obtained from the company within a few days.

(II) Preparation of midiprep BAC DNA by alkaline lysis method (1 day):

Reagents:

1. Solution I: 50 mM glucose, 25 mM Tris.HCl (pH 8.0); 10 mM EDTA (pH 8.0)

2. Solution II: 0.2N NaOH, 1% SDS (0.4 g NaOH, 45 ml ddH2O, 5 ml 10% SDS).
3. Solution III: 5M KOAc (60 ml), glacial acetic acid (11.5 ml), H2O (28.5 ml).

Protocol:

1). Inoculate each BAC containing bacterial to 50 ml LB containing 12.5 ug/ml chloramphenicol. Grow overnight in 37° C.
2). Spin the overnight culture in a 50ml Falcon tube for 20 min. at 3500 RPM at 4° C. Pour off the supernatant.
3). Resuspend the pellet in 1 ml cold solution I. Transfer the cell mix to a 15 ml polybrene centrifugation tube and place on ice for 5 min.
4). Then add 2 ml fresh (<2 weeks old) solution II. Mix well by inverting vigorously a few times.
5). Immediately add 1 ml cold solution III, mix by inverting gently several times, and place on ice for 10 min (this solution may be left overnight).
6). Spin at 10,000 rpm for 12 min. at 4° C. Transfer the supernatant to a new polybrene tube.
7). Add 4 ml Phenol (pH6.0)/Chloroform (1:1), and mix well by inverting the tube several times. Spin again at 10,000 rpm for 12 min. at 4° C.
8). Transfer the upper layer to a new tube, and add 8 ml 100% ethanol to it. Invert the tube vigorously several times to mix well. Spin at 10,000 rpm for 30 min at 4° C. It can also be kept in −20° C. for overnight prior to centrifuging.
9). Wash the pellet with 70% ethanol. Dry by vacuum and resuspend the DNA in 200 ul TE. The BAC midiprep DNA may be stored in 4° C. for months (Do not freeze the BAC DNA, since repetitive freezing and thawing will result in degradations).

(III) BAC maxiprep DNA preparation:

Two methods were used to prepare large quantities of RNA-free BAC maxiprep DNA. The first method is the standard cesium chloride banding method (see Maniatis, supra). This method was used routinely to obtain >500 ug BAC DNA from 1 liter bacteria culture. The second method, uses a commercially available column, the Nucleobond AX-500 (made by The Nest Group, Southborough, Mass.). The maxiprep DNA are also stored in 4° C. for long-term storage.

(IV) Mapping the BACs by Pulsed Gel Electrophoresis and Southern blots (3–5 days):

To determine the size of each BAC and to confirm that the BAC contains the gene of interest, a simple mapping of the BACs is done. The following enzymes are used to map each BAC: Not I (to release the BAC insert), Mlu I, NotI/Mlu I (double digest), PmeI, PmeI/NotI and XhoI. Digestion is done in a 40 ul total volume, which contains the following: 5 ul midiprep DNA, 4 ul digestion buffer, 4 ul 10×BSA (if necessary), 1 ul 100 mM spermidine (final concentration 2.5 mM), 2 ul enzyme (10–40 units), and ddH2O. Digestion is done at 37° C. for >5 hrs.

The digested BACs are resolved on a pulsed field gel (Bio-Rad's CHEF-DRII). The gel is 1% agarose in 0.5× TBE. The gel is run in 0.5×TBE. The separation condition is the following: 6v/cm, 5s to 15s linear ramping for 15 hrs to 18 hrs at 14° C. The New England Biolab's PFGE marker I or II as the high molecular weight marker and 1 kb DNA ladder (Life Technologies Inc.) as the low molecular weight marker are used.

The gel is then stained with ethidium bromide (1 to 5000, or 1 to 10,000 dilution of 10 mg/ml stock) for 30 min prior to taking the photograph. Then the gel is blotted onto the nitrocellulose membrane and hybridized to cDNA and genomic DNA probes according to standard protocols (Maniatis, supra). To ensure the entire cDNA is included in the BAC, probes/or oligonucleotides from both the 5' end and the 3' end of the gene are used to probe the blot separately. Those large BACs containing the entire gene are usually selected for BAC modification.

2. Construction of the Shuttle Vector with the Recombination Cassette

Since targeted BAC modification is a method based on homologous recombination, homologous sequence from the BAC has to be obtained. Two homologous sequences of about 500 bp each (namely A and B, FIG. 7) is all that is needed to construct the shuttle vector for BAC modification. The homologous sequences are chosen such that a given modification (i.e. insertion, deletion and point mutation) will be introduced between A and B in the BAC. A and B can be obtained by direct sequencing of the BACs. The sequencing oligonucleotides are designed based on the cDNA sequence.

(I) Direct sequencing of the BAC (2–3 days):

1) If maxiprep DNA is used, go directly to step 2. If midiprep DNA is used, first add 100 ul ddH2O and 10 ul 10 mg/ml RNAse A to 100 ul midiprep BAC DNA, and incubate at 37° C. for >1 hr. (This step is critical, incomplete RNAse treatment will result in poor precipitation and sequencing).
2) Add 132 ul PEG mix (2.5M NaCl and 20% PEG 8000) to the treated DNA. Put on ice for 5 min.
3) Spin for 15 min at 4° C. Discard the supernatant. Spin again for 2 min. Completely remove the remaining supernatant, which contains the PEG mix.
4) Wash the pellet with 70% ethanol. Dry in Speedvac and resuspend in 20 ul ddH2O.
5) Run 2 ul on a agarose gel to estimate the final concentration. Usually use 6–8 ul (500 ng–1000 ng) DNA for automatic sequencing, also use 150 ng sequencing oligos.

Each sequencing reaction will result in up to a 500 bp sequence. Sequence more than one BAC for a given primer to compare the sequences. The main purpose for sequencing is to design a 20 bp PCR primer, which is about 500 bp away from the sequencing oligo (which usually is the other PCR primer), to enable PCR amplification of this genomic fragment and to clone it into the building vector. Therefore, as long as a 20 bp sequence can be identified which is at the appropriate position, and which is the same in several independent sequencing reactions, the goal is achieved. The quality of the DNA sequence in between is not very critical.

(II). Vectors used in targeted BAC modification:

A two vector system is designed to construct the shuttle vector for BAC modification (FIG. 1). The first vector is a pBS.KS based building vector, which is used to construct the recombination cassette containing homologous sequence A and homologous sequence B and the modification to be introduced between them. The recombination cassette was not constructed in the pSV1.RecA shuttle vector was for the following reasons: first, it is a low copy plasmid so that it is difficult to obtain high quantity DNA; second, it is a large plasmid (11 kb), so it is relatively difficult to clone. The building vector contains the marker gene to be introduced into the BAC, cloning sites flanking it (usually EcoRI for cloning the homology A and XbaI for homology B, and rare restriction sites such as MluI, PmeI and Pac I for mapping of the modified BAC). There are two Sal I sites (or one Sal I, one XhoI) flanking the multiple cloning sites. They are used to release the recombination cassette and subclone it into the Sal I site of the pSV1.RecA vector, to complete the shuttle vector construction. One thing about designing the building vector is that there should not be any Not I sites within the recombination cassette, since NotI sites are used in the end to release the linear modified BAC for biological experiment (e.g., pronuclear injection). The map and utility of various building vectors and the shuttle vector are described below.

(A) Building Vectors (pBV) All Based on pBS.KS (Stratagene)

pBV.IRES.LacZ.PA (FIG. 9) This vector is designed to introduce lacZ marker gene into a coding exon or the 3' UTR of a given gene, to study gene expression and gene regulation in vivo. IRES will enable the translation of the marker gene independent of the endogenous translation initiation codon.

pBV.EGFP1 (FIG. 10) This vector is designed to introduce the brighter version of the green fluorescent protein, EGFP1 (Clontech), into an exon of a given gene before the endogenous ATG or fused in frame with the endogenous gene. The green fluorescent protein will mark gene expression in living cells and living organisms. Since the marker gene does not contain its own polyA addition sequence, the endogenous polyA sequence is used.

pBV.IRES.EGFP1 (FIG. 11) This vector is used to introduce EGFP1 gene into the coding region or the 3' UTR of a given gene, with its translation independent of the endogenous translation frame.

pBV.pGK.Neo.PA (FIG. 12) This vector is designed to introduce a neo expression cassette into the BAC, containing the neo gene with the pgk promoter and the polyA addition signal. Modified BAC can be introduced into tissue culture cell lines (i.e. ES cells) to obtain stable transfected cells by selecting for neomycin resistance. This vector is particularly useful for gene targeting with modified BACs. Notice that although there are two identical pgkpA sequence at the 3' end of the neo gene, it will not interfere with the proper expression of the neo gene. The only consequence is that during BAC modification, one of the pgkPA sequence may be deleted due to homologous recombination.

Figure 8:
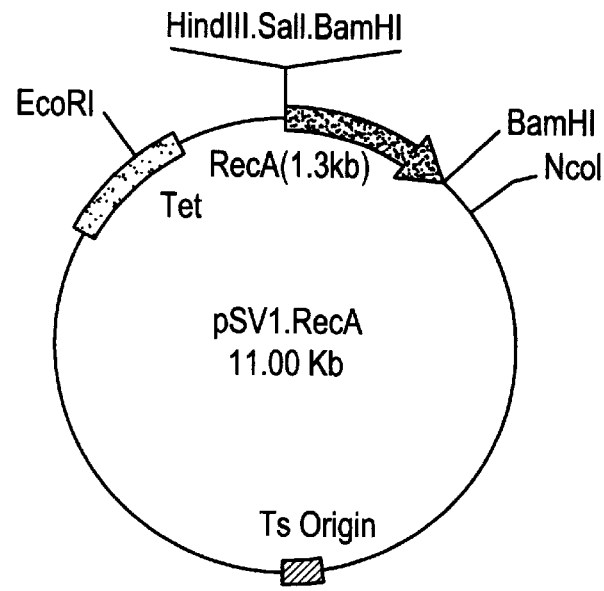
FIG. 8 is the restriction map of pSV1.RecA. This temperature sensitive shuttle vector is based on the pMBO96 vector originally constructed by M. O'Connor et al. [*Science*, 244:1307–1312 (1989)].

(B) Temperature Sensitive, Recombination Inducing Shuttle Vector (pSV1.RecA) (FIG. 8)

This plasmid vector was modified from the pMBO96 vector originally constructed by O'Connor et al (Science, 1989, Vol 244, pp. 1307–1312). The pMBO96 vector was a gift from Dr. Michael O'Connor. The original vector carries tetracycline resistance, and contains a pSC101 temperature sensitive origin of replication, which allows the plasmid to replicate at 30° C. but it will cease replication and is lost at 43° C. The E. coli RecA gene was amplified by PCR and subcloned into the Bam HI site, to create the pSV1.RecA vector. The Sal I site is used to subclone the recombination cassette from the building vector.

(III) Cloning two PCR amplified BAC fragments into the building vector (6–8 days):

The first step of targeted BAC modification involves the subcloning of two small genomic fragments (A and B) into an appropriate building vector, which includes two steps of conventional sub-cloning. One should pay attention to the following points when designing the A and B fragments.

1. Each fragment should be >500 bp (the shortest attempted was 450 bp). PCR amplified fragment with appropriate restriction sites designed at the end of the PCR primer is the method of choice. Frequently, an additional restriction site is designed into one of the two PCR primers to assist in determining the orientation of the cloned PCR fragment. The relative imprecision of PCR amplification does not appear to affect the BAC modification efficiency.

2. As mentioned before, neither A nor B fragments should containing internal XbaI, EcoRI and Sal I sites, since these sites will be used for subcloning. Nor should they contain NotI sites since NotI is used to linearize the BAC 3. The orientation of the arms must be preserved as in the endogenous loci.

(IV) Subcloning the recombination cassette from the building vector into the pSV1.RecA shuttle vector (4 days):

1. Prior to cloning the recombination cassette into the shuttle vector, the following plates are usually prepared: the tetracycline (10 ug/ml) LB agar plates and the tetracycline (10 ug/ml)+chloramphenicol (12.5 ug/ml) LB agar plates. Plates are made according to standard protocol [Sambrook et al., (1989) supra].

2. Prepare pSV1.RecA and building vector midi-prep DNA by the alkaline lysis method (see above). For the pSV1.RecA vector, Qiagen columns can also be used to obtain high purity DNA, though yield is usually low. This is due to the low copy number of the pSV1 plasmid. For preparation of pSV1.RecA DNA, the culture should be grown at 30° C. in LB+tetracycline (10 ug/ml). The final midi-prep DNA is usually dissolved in 200 ul TE or ddH$_2$O.

3. Digest 2–5 ug of the pSV1.RecA and pBV with Sal I. For pSV1.RecA, the reaction is done in 200 ul volume:
100 $\mu$l medi-prep DNA (2–5 ug) or
20 $\mu$l of Qiagen midi-prep of pSV1.RecA
20 $\mu$l H buffer (Boehringer Mannheim)
8 ul Rnase (10 mg/ml) (for alkaline lysis preps)
10 ul Sal I (200 units, Boehringer Mannheim)
62 ul ddH$_2$O The reaction is performed at 37° C. for >6 hours (usually overnight), then 30 units more Sal I is added, and the digestion continue for another 1–2 hours. (Optional) A small sample of the digestion (5 ul) may be run on a gel to ascertain that a complete digestion has been achieved.

4. (Optional) At the end of the digestion, Sal I is inactivated by heating to 65° C. for 15 minutes.

5. The vector is then treated with alkaline phosphatase by adding 20 ul 10×dephosporylaiton buffer, 4 ul (1 unit/ul) calf intestinal alkaline phosphatase (Boehringer Mannheim) for 30 minutes at 37° C. The enzyme is then inactivated by adding 20 ul 50 mM EDTA (to a final concentration of 5 mM), and heating at 75° C. for 15 minutes.

6. The digested pSV1 vector and pBV with recombination cassette are run on a 1% low melting Seaplaque GTG agarose at 75 V for 8–10 hours. The DNA should be run in a large well created by taping together several teeth of the comb.

7. An 11 kb linearized plasmid band should be visible on the gel for pSV1.RecA. Cut this band and also the recombination cassette insert band from the gel. Purity these DNA fragments using Geneclean Spin columns (Bio 101, Inc.) according to manufacture's direction. Run a small portion of the purified DNA on a gel to estimate the DNA concentration.

8. Ligation reaction: Each ligation reaction is done in 20 ul total volume containing: >50 ng pSV1.vector, 100–200 ng insert, 2 ul 10× ligation buffer (Boehringer-Mannheim), 2 ul 10 mM ATP, 1 ul ligase (Boehringer-Mannheim) and ddH2O. Ligation is carried out at 16° C. overnight.

9. Transformation of DH5a competent cells with pSV1 vectors: Half of the ligation reaction (10 ul) is used for transformation, by adding to 100 ul of cold, chemical-induced DH5a competent cells. Incubate 15 minutes on ice, then heat shock at 37° C. for 2 minutes, add 1 ml LB to the tube, and shake at 30° C. for 30 minutes. The cells are then centrifugated at 6000×g for 4 minutes and the pellet is resuspended in 100 ul LB and spread onto Tet (10 ug/ml) LB agar plates. Incubate the plates at 30° C. for >15 hrs hours.

11. Pick colonies and do colony hybridization according to standard protocols [Sambrook et al., (1989), Supra], probing with a fragment derived from the pBV1, such as homology arms (A or B) or the marker gene. Positive clones are further analyzed by restriction digest, and if necessary, Southern blots.

3. Targeted BAC Homologous Recombination in Bacteria (I) Equipment

Bacterial incubator: set either at 30° C. or at 43° C.

Shakers: set either at 30° C. or at 43° C.

(II) Reagents and Plates

The following reagents and plates should be prepared prior to the targeted modification experiment. All the plates can be stored in 4° C. for up to one month. Detailed methods for preparation of various antibiotic resistant plates can be found in Maniatis.

1. Tetracycline stock solution (1000×): 10 mg/ml in 50% ethanol, wrapped in aluminum foil and stored in −20° C. for up to one month.

2. Chloramphenicol stock solution (1000×): 12.5 mg/ml, dissolved in ethanol (>50%), stored in −20° C.

3. Tetracycline plates (tet plates): LB agar plates containing 10 ug/mil tetracycline. Store in 4° C. and wrapped in aluminum foil to avoid the light.

4. Chloramphenicol plates (Chl plates): LB plates contain 12.5 ug/ml Chloramphenicol.

5. Tetracyline+Chloramphenicol plates: LB plates contain 10 ug/mil tetracycline and 12.5 ug/ml chloramphenicol.

6. Fusaric acid+Chloramphenicol TB plates (FA+Chl plates): Prepared as following.

First, make tryptone broth agar, or TB agar:

|  | 500 ml TB | 1 L TB |
| --- | --- | --- |
| Tap $H_2O$ (not distilled $H_2O$) | 500 ml | 1 L |
| Bacto tryptone | 5 g | 10 g |
| Yeast extract | 0.5 g | 1 g |
| Glucose | 0.5 g | 1 g |
| NaCl | 4 g | 8 g |
| 0.1 M $ZnCl_2$ | 0.25 ml | 0.5 ml |
| Chlorotetracycline (6.3 mg/ml) | 4 ml | 8 ml |
| Bacto agar | 7.5 g | 15 g |

Autoclaving the above TB. Also autoclave 500 ml of 1M $NaH_2PO_4.H_2O$. After autoclave, wait till the TB agar drop to about 60° C., then add the following:

|  | 500 ml TB | 1 L TB |
| --- | --- | --- |
| $NaH_2PO_4.H_2O$ (1 M) | 36 ml | 72 ml |
| Fusaric Acid (2 mg/ml, filter ster.) | 3 ml | 6 ml |
| Chloramphenicol (12.5 mg/ml) | 0.5 ml | 1 ml |

Pour the plates and leave the plates outside overnight and then store at 4° C. There is no need to avoid the light.

(III) Making competent BAC containing bacteria (1 day):

A chemical method is used to prepare competent cells from BAC containing bacteria host (Inoue et al, Gene 96, p23–28, 1990).

(1) Media and plates:

LB+Ampicilin (50 ug/ml) agar plates;

TB media (10 mM Pipes, 55 mM $MnCl_2$, 15 mM $CaCl_2$ and 250 mM KCl), all the components except for $MnCl_2$ are mixed and the pH is adjusted to 6.7 with KOH. Then, $MnCl_2$ was dissolved, the solution was sterilized by filtration through a 0.45 u filter unit and stored at 4° C. All salts were added as solids.

(2) Frozen stock of BAC containing DH10B cells were taken by a metal loop and inoculated into 3 ml of LB+chloramphenicol (12.5 ug/ml). Grow the culture with rigorous shaking in 37° C. for overnight.

(3) Take 0.5 ml overnight culture, add to 50 ml LB+chloram. (12.5 ug/ml) and grow at 37° C. with rigorous shaking till an optical density at 600 nm of about 0.6 is achieved.

(4) Place the flask on ice for 10 min. Then transfer to a 50 ml falcon tube and centrifuge at 3000 rpm for 10 min at 4° C.

(5) Pour the supernatant. Resuspend the pellet in 16 ml ice-cold TB. Incubate on ice for 10 min, then spin again as above.

(6) The cell pellet was gently resuspend in 4 ml of TB supplemented with 7% DMSO. Incubate on ice for 10 min, then dispense 0.5 ml aliquot and immediately frozen by immersion into liquid nitrogen. The tubes are stored in −80° C. for further use.

(IV) Co-integrate formation and identification through Southern blot analyses (4 days):

1. Transform the competent BAC cells with the Ts shuttle vector, using 10 ul of the midiprep DNA and 200 ul BAC containing competent cells. Transformation is done as in (IV) of part 11. Plate 1/10 of the transformed cells onto Tet+Chl plates, and grow overnight at 30° C.

2. To generate co-integrates, single colonies (up to 6 in total) is picked up with a sterilized metal loop and diluted each into 1 ml LB. Vortex to disperse the bacteria in LB. Plate 100 ul LB+Bacteria on to two Tet+Chl plates. Incubate one at 43° C. incubator, and incubate the other at 30° C. overnight.

3. A thick lawn of bacteria will grow on the plates incubated in 30° C. For the plates incubated in 43° C., only dozens of individual colonies will grow on top of a hazy background of very small satellite colonies. Pick 20 of these large colonies, inoculate each colony to 2 ml LB supplemented with tet (10 ug/ml) and chloramphenicol (12.5 ug/ml), and streak the same colony onto a tet+chl plates. Grow the miniculture with rigorous shaking at 43° C. overnight. Incubate the master plate at 43° C. incubator overnight and stored in 4° C. for further use.

4. Make miniprep DNA from a 1.5 ml miniculture using standard alkaline lysis methods. Dissolve the DNA in a 30 µl TE and use 5–10 µl of the DNA for restriction enzyme analysis.

5. Restriction digest with appropriate enzymes and analysis of the co-integrate by Southern blot. Due to the high efficiency of co-integrate formation even with 500 bp homology (>10%), I usually only analyze co-integration on one homology side (either A or B). For example, to analyze co-integrate on A side, use fragment A as a probe and digest the BAC DNA with an enzyme that will detect the co-integrate formation on A side (such as EcoRI). Standard southern blots are done to reveal the co-integrates. As controls, the original BAC and the shuttle vector should be included in this analysis. The reason to use the homology arms as Southern blot probes is that it will hybridize to two bands of appropriate size in the co-integrate BAC. As controls, the original BAC and the shuttle vector should be included in this analysis.

(V) Resolution and Southern blot analyses of correctly resolved BACs (6 days):

1. Once the co-integrates are identified, a purified single colony of the co-integrate from the Tet+Chl plates grown at 43° C. is picked and streaked onto a Chlorampenicol plate (12.5 ug/ml)) to grow single colonies.

2. Incubate the Chl plate at 43° C. overnight, to allow some bacteria to resolve and to lose the temperature sensitive pSV1 plasmid, and hence lose the tet resistance gene.

3. To select for tet sensitivity in the resolved BAC, 8 to 16 single colonies from the Chl plate are picked, and streaked onto Fusaric acid+Chloramphenicol plate (2 to 8 individual colonies can be streaked onto each plate). Two controls can be done to test the effectiveness of antibiotic selection of the FA+Chl plates: one is streaking a Tet-resistant colony (from the Tet+Chl plate), and the second is a tet-sensitive colony (from the plate growing the original BAC). Another control can be done is to streak the co-integrate colonies on just Chl plate (without fusaric acid).

4. Incubate the FA+Chl plates at 37° C. for 2–3 days. A long incubation time is necessary since the resolved colonies grow very slowly due to the presence of the fusaric acid. Tet containing colonies should not grow even in 48 hrs incubation. Therefore, there should be much fewer colonies on the Chl+Fusaric acid plates than on the Chl plates. These colonies are the resolved colonies.

5. A) Two alternative methods can be used to identify the correctly resolved BACs. If both A and B homology are about the same length, one can just pick 10–20 colonies, prepare miniprep DNA by alkaline lysis and do Southern blot to analyze the targeting events. About half of the resolved BACs should contain the correctly targeted marker genes. B) If the two homology arms are not the same length (>500 bp difference), one should use the colony hybridization to select the correctly resolved BACs. Pick 50–100 individual colonies from FA+Chl plates, streak them onto Chl plates and also onto the Tet+Chl plates, as a control for Fusaric acid selection. Each plate can accommodate 50 test colonies and two positive control colonies, which are the co-integrate colonies from the Chl plate. Grow the colonies overnight at 37° C. Abundant colonies should grow on the Chl plate, and none on the Tet+Chl plate, except the positive co-integrate controls. The selection for tet sensitivity at step 4 is very stringent and has essentially no background. Therefore, all the colonies that grow on FA+Chl plates have been found to contain resolved colonies. Colony hybridizations is performed, according to the standard protocols [Sambrook et al., (1989) supra], to select for the colonies that are resolved and resulted in targeted modification. The colony hybridization probe should be part of the recombination cassette excluding the arms, such as lacZ, Neo, GFP or polyA sequences.

6. Midi-prep DNA are prepared for the positive clones by the alkaline lysis method as described above. Restriction digests and Southern blots are performed to confirm targeting event on both homology side (A and B).

7. Pulse field gel analyses should be done to confirm the modification event and to determine if there are any rearrangements in the modified BACs. Since there are two Not I site flanking the BAC insert (Research Genetics), digestion with Not I should reveal the size of the modified BAC. Generally MluI, PacI and PmeI sites are included in the recombination cassette. Digestion with these enzymes will confirm the targeting events. Double digestion with these enzymes and with Not I will help to determine the integration site of the recombination cassette in the BAC. XhoI is usually used to fingerprint the modified BAC, since it has a wide distribution of fragment sizes. Comparing the Xho digestion pattern of the modified BAC with the original BAC will reveal any gross rearrangements in the modified BAC. Other enzymes, such as BamHII and AvrII can also be used for this purpose. Targeted BAC modification has been found not to introduce any unwanted rearrangements into the BACs. Probes used to hybridized to the PFGE blots include: insert specific probes (s.a. lacZ, PolyA, GFP and Neo) and whole BAC probe (to reveal all the digested bands from the BAC). Once the modified BACs are confirmed to have the specific targeted modification events and the lack of rearrangements, these BACs are ready to be used for the biological experiments, such as producing transgenic mice or transfecting cells.

4. Preparation of Large Quantity, High Quality Linearized BAC DNA for Pronuclear Injection (I) Maxiprep BACDNA preparation (1 day):

See the isolation and initial mapping of BACs section above.

(II) Prepare intact linearized BAC DNA for pronuclear injection (1 day):

1. Digest 50 ug cesium banded BAC maxiprep DNA overnight in 500 ul total volume containing:
   50 µg DNA
   50 µl 10×NotI buffer or Buffer 3 (NEB)
   50 µl 10×BSA
   12.5 µl 100 mM Spermidine (final concentration 2.5 mM)
   25 µl (250 units) Not I (NEB)
   ddH2O to 500 ul total volume
   Digestion is carried out at 37° C. for >10 hrs.

2. Preparation of the CL4b Column (performed at room temperature): Take a 5 ml plastic pipette, air-blow the cotton to the tip and clamp the pipette on a stand. Shake the CL4b sepharose (Phamacia) well, and gradually add the sepharose into the plastic pipette. Add until the packed sepharose to almost the top (with about 1 ml space to spare). Never let the column dry.

3. Once the column is ready, use a 10 ml syringe to set a reservoir on top of the column (buffer is added to the reservoir). Then equilibrate the column with 30 ml of the injection buffer (10 mM Tris.HCl,pH7.5, 0.1 mM EDTA and 100 mM NaCl). This takes about 2–3 hours.
4. Now add 5 ul 10×DNA dye into the 0.5 ml digested BAC DNA. Take the reservoir out and gently add the DNA(+dye) onto the top of the column with a pasteur pipette. Wait until the DNA+dye just goes into the column, gently add 0.5 ml of injection buffer on top of the column.
5 Once the injection buffer almost goes in, the reservoir is put back with 10 ml of injection buffer in it. Now start collecting 0.5 ml fraction with a 24 well plate. Generally about 12 fractions are collected (or until the blue dye is almost at the bottom of the column).
6. Run 50 ul of each fraction on a pulse field gel to identify the appropriate fractions. The bands should be visible after ethidium bromide staining. A Southern blot is performed in order to choose the fractions with highest yield, and the least degradations.
7. Purified DNA is stored at 4° C. It is stable for weeks (e.g., no degradation was detected after 3 weeks).

Results

BACs are useful as tools for studying the regulation of gene expression in vivo. In one particular example, a BAC can include the murine brain specific zinc finger gene, RU49 [Yang et al., Development 122:555 (1996)]. RU49 has been shown by in situ hybridization to be expressed in the granule cell population of the murine cerebellum, the dentate gyrus and the olfactory bulb in the brain. However, proper expression of the lacZ marker gene could not be obtained in the cerebellum with a 10 kb RU 49 promoter-lacZ construct in transgenic mice, e.g., only one out of ten lines showed partial expression in the cerebellum. To overcome this problem, an homologous recombination based method for inserting an IRES-lacZ marker gene into the BAC containing RU49 was developed. The germline transmission in transgenic mice of an intact modified BAC and proper expression of the lacZ transgene in the cerebellum is demonstrated.

To modify BACs in E. coli, a temperature sensitive shuttle vector based system for homologous recombination was employed [O'Connor et al., Science 244:1307–1312 (1989); Hamilton et al., J. Bacteriol. 171:4617 (1989)]. This temperature sensitive plasmid will replicate in cells growing at the permissive temperature (30° C.), but will be lost in cells growing at the restrictive temperature (42–44° C.) because its origin of replication can not function at the restrictive temperature [Hashimoto-Gotoh et al., J. Bacteriol. 131:405–412 (1977)]. To overcome the recombination deficiency of the BAC host i.e., a RecA⁻ host cell, the E. coli recA gene was introduced into the temperature sensitive shuttle vector. When transformed with the temperature sensitive shuttle vector (carrying a recombination cassette containing the recA gene) the host strain becomes conditionally competent to perform homologous recombination allowing in vivo modification of the resident BAC.

The general strategy for targeted BAC modification is shown in FIG. 1, which illustrates the steps involved in inserting a marker gene, e.g., IRES-lacZ-pGKpolyA (ILPA), into the BAC. First, two small genomic fragments, e.g., A and B, each containing greater than 500 basepairs of a gene of interest are cloned into the building vector (pBV1) in appropriate order and orientation to generate the recombination cassette. The recombination cassette is then transferred into the temperature sensitive shuttle vector (e.g., pSV1.RecA). The reason the recombination cassette is not built directly in the shuttle vector is due to the relative difficulty in manipulating its DNA, due to low copy number [Bochner et al., J. Bacteriol. 143:926 (1980); Maloy et al., Bacteriol. 145:1110 (1981)] and large vector size (11 kb).

This shuttle vector is then transformed into E. coli containing the BAC. The transformants can be selected by tetracycline resistance (carried by pSV1.RecA) and chloramphenicol resistance (carried by the BACs) at 30° C. Since the shuttle vector also carries the recA gene, homologous recombination can occur between the shuttle vector and the BAC, through either homology at A or B to form co-integrates. The co-integrates are selected by growth on tetracycline and chloramphenicol plates at 43° C. This temperature is non-permissive for shuttle vector replication, so that the non-integrated, free shuttle vectors are lost, resulting in the selection for bacteria carrying the integrated shuttle vectors, (either into the BACs or into the bacterial chromosomes). Correct BAC co-integrates can be identified by Southern blot analyses.

The co-integrates are then restreaked onto the chloramphenicol plates and grown at 43° C. overnight. A fraction of the co-integrates will undergo a second recombination event (resolution), through either homology at A or B. The resolved BACs will automatically lose the tet and the recA genes, since the excised shuttle vector plasmids cannot replicate at the non-permissive temperature. The resolved BACs can be selected by growing on chloramphenicol and fusaric acid plates at 37° C., as growth on fusaric acid plates selects for the loss of tetracycline resistance, i.e., counterselecting against BACs that are resistant to tetracycline. As illustrated in FIG. 1, depending on which pair of homologous fragments undergo the second recombination event, the resolved BAC can be either the original BAC or the precisely modified BAC. The desired clones can be identified by colony hybridization using a labeled probe for the inserted marker. One important aspect of the method is that the recA gene is only temporally introduced into the bacterial host. Once the modification is finished, the bacteria will automatically lose the recA gene, returning to the recombination deficient state suitable for stable maintenance of the modified BACs.

Figure 2A:
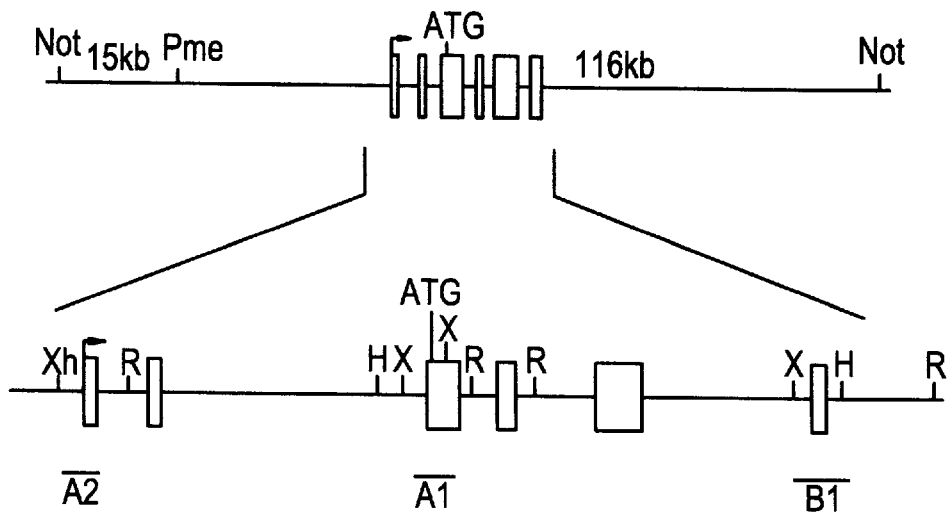
FIGS. 2A and 2B show a schematic representation of targeted modifications of the BAC 169, which contains the murine zinc finger gene, RU49. BAC169 containing RU49 was obtained from screening of the mouse 129 strain BAC genomic DNA library (Research Genetics).
Figure 2B:
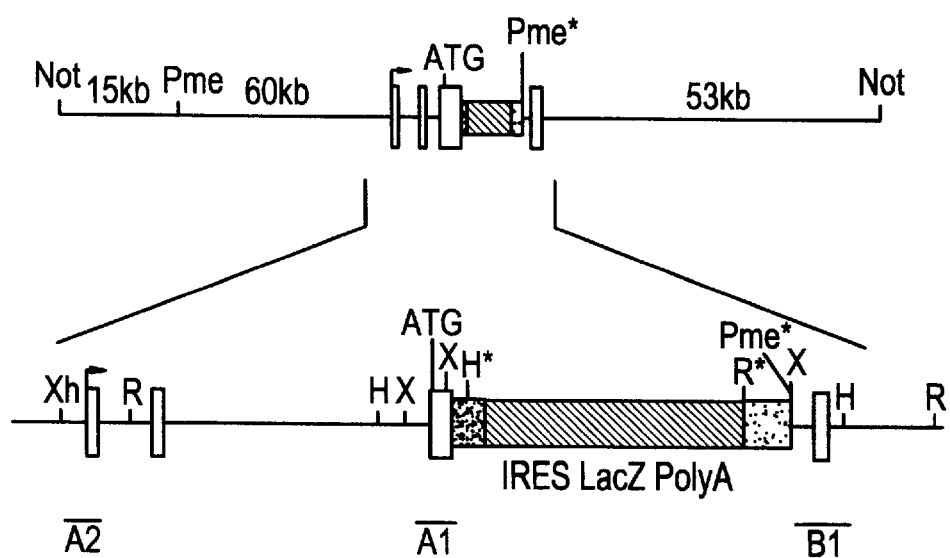
Figure 3A:
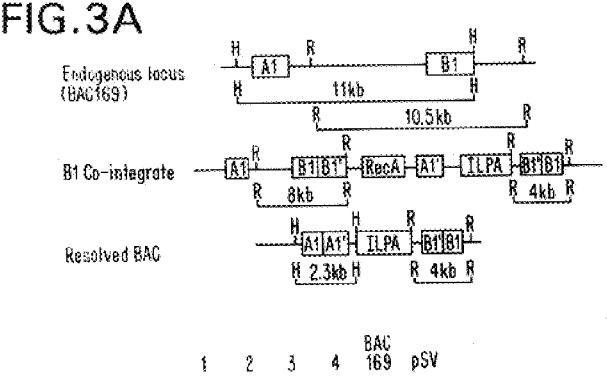
FIGS. 3A–3D show Southern blot analyses of BAC co-integrates and resolved BACs.
Figure 3C:
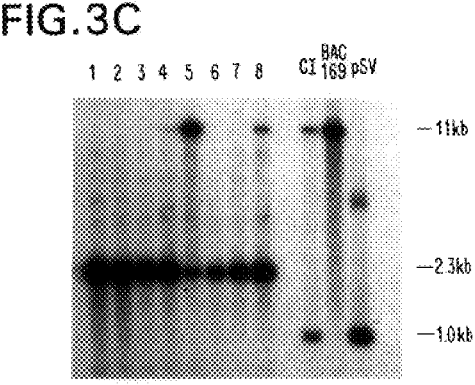
Figure 3B:
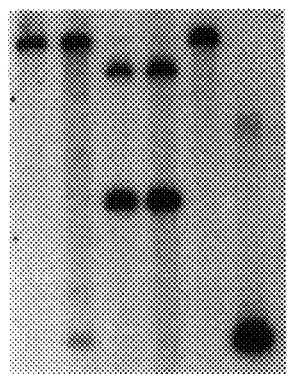

This strategy termed targeted modification of BACs, was tested by introducing the IRES-lacZ-polyA (ILPA) marker into the 131 kb murine BAC169 containing the RU49 locus (FIG. 2A). In this case, the marker gene to the first coding exon of the RU49 gene was targeted with homology fragments being 1 kb and 1.6 kb respectively (FIG. 2B). Placing the IRES sequence before the lacZ gene ensures the translation of the marker gene even when lacZ gene is placed after the translation start site [Pelletier et al., Nature 334:320 (1988)]. The pSV1.RecA temperature sensitive shuttle vector containing the recombination cassette was transformed into the DH10 E. coli strain containing the BAC169 and selected by growth at either 30° C. or 43° C. on plates containing chloramphenicol and tetracycline. In contrast to growth at 30° C., which produced a thick lawn of transformed cells, growth at 43° C. resulted in growth of individual colonies. Twenty of these were picked and tested by Southern blots for co-integration of the shuttle plasmid into BAC169. As shown in FIG. 3B, analysis of twenty clones using the B1 fragment of the RU49 homology cassette resulted in the identification of two clones containing the appropriate 4 and 8 kb EcoRI bands (10%), indicating that these clones carry co-integrates that have occurred through this region of homology.

Figure 3D:
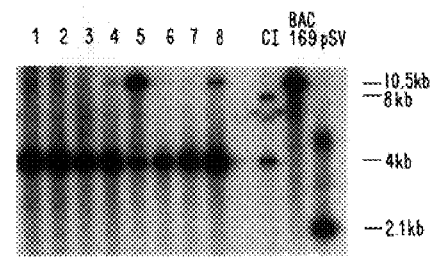

The co-integrates are then resolved as described above by growing the cells first on chloramphenicol plates at 43° C. and then on chloramphenicol and fusaric acid plates at 37° C. Fusaric acid provides a strong counterselection against bacteria containing the tetracycline resistance gene. Indeed, 200 colonies picked from these plates were all tet sensitive, indicating the stringency of the selection. Duplicated colonies growing on the chloramphenicol plates were used for colony hybridization with the pgkpolyA probe. Eight out of 200 colonies were positive (4%). Southern blot analyses using either homology at A1 or B1 as the probe showed that all these clones contained correctly resolved BACs (FIGS. 3C and 3D). Three BACs (lanes 4, 5 and 8) also contained wild type bands, which may represent either contamination from other clones, or a BAC containing two copies of co-integrates that resolved through two different homologous regions.

Figure 4A:
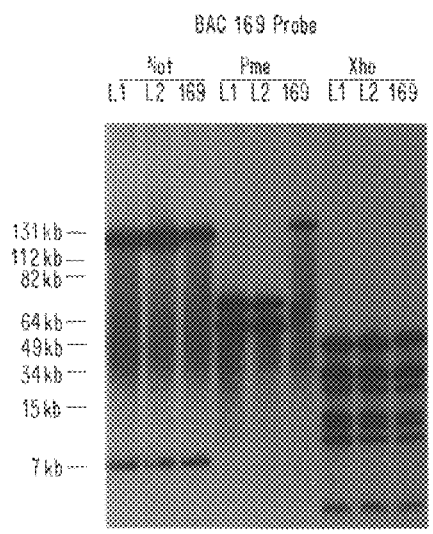
FIGS. 4A–C show pulsed field gel electrophoresis analyses of modified 169 with the ILPA insertion. DNA for two independent clones of BAC169. ILPA (L1 and L2) and BAC169 were prepared by alkaline lysis, and then digested with NotI, PmeI and XhoI (in a standard buffer supplemented with 2.5 mM spermidine). The digested DNA were separated by pulsed field gel electrophoresis (Bio-Rad's CHEF-DRII, 5 to 15s, 15 hours at 14° C.) and blotted on to nitrocellulose filter (Stratagene). The same filter was probed separately with three probes. L1 and L2 are lacZ1 and LacZ2 which are independent clones which correspond to clones 1 and 2 respectively in FIGS. 3C and 3D.
Figure 4B:
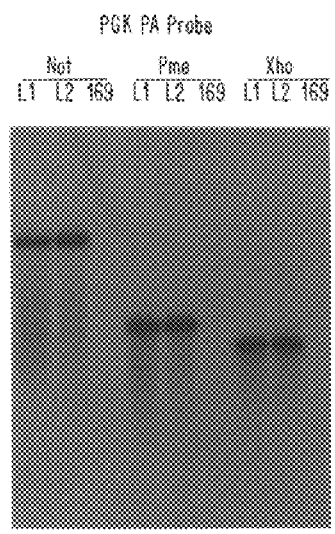
Figure 4C:
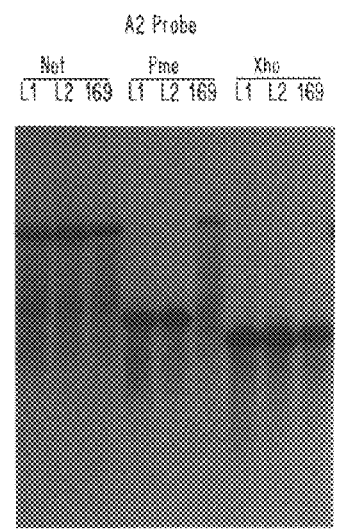

The next step in our analysis was extensive mapping of the modified BACs to determine whether any unexpected deletions or insertions were generated during the modification procedure. FIG. 4 shows pulsed field gel mapping of the modified BAC L1 and L2 and the original BAC 169. The same filter was probed separately with the whole BAC169 probe, with a probe from the inserted marker gene (pgkpolyA) and a probe from the 5' non-modified region of the RU49 gene (A2). BAC169 probe (left panel) hybridizes with all the restriction fragments for each BAC. Thus, XhoI digestion reveals a finger print of the modified BACs showing that essentially all fragments are preserved. The only difference is that the fragment containing the ILPA insert is slightly smaller than the corresponding wild type fragment due to the replacement of the 7 kb RU49 fragment with the 4 kb marker gene (FIG. 2B). Digestion with NotI, which releases the entire BAC insert, also reveals a slightly smaller DNA insert in modified BACs for the same reason. Since the marker gene was engineered to carry an additional PmeI site (FIG. 2), digestion of the BAC L1 and L2 DNAs with this enzyme results in the generation of two fragments, in contrast to the single fragment seen in the original BAC69. The sizes of these fragments allow the determination that these BACs contain approximately 75 kb 5' to the PmeI site, and 53 kb 3' to it (FIG. 2). No apparent rearrangements have occurred during the modification procedure.

To confirm this conclusion, the modified BACs and BAC169 were probed with both a marker specific probe (pgkpolyA) and a probe near the promoter region and outside the modification region (A2). Consistently, both modified BACs contained a single band homologous to the marker gene probe which is not present in BAC169. When the A2 probe was used, a single band of expected size appeared in all three BACs. Additional fingerprinting of all eight modified BACs with HindIII, EcoRI and AvrII digests showed that no detectable rearrangements or deletion existed in these BACs. Thus, the temporary introduction of the recA gene into the BAC host strain does not introduce any rearrangements or deletions.

To test the reproducibility and reliability of the targeted BAC modification, the BAC L1 was further modified by replacing the IRES-lacZ sequence with pgk-neo sequence. In this case, homologous fragments of about 500 bp each were used. The modified BACs were also efficiently obtained and shown not to have any rearrangements or deletions. Therefore, targeted BAC modification is a simple method to precisely modify BACs without introducing any unwanted changes in the BACs.

Figure 5A:
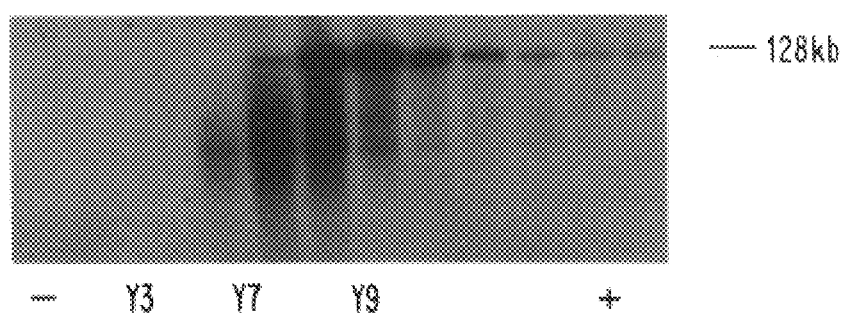
FIGS. 5A–E show the production of BAC transgenic mice.

To demonstrate the possibility of using the modified BACs for in vivo studies for gene expression and gene function, transgenic mice carrying the modified BAC169 with the IRES-LacZ insertion were generated. To purify the 128 kb BAC insert for pronuclear injection, several established methods for purifying large YAC DNA were attempted, and resulted in considerable amount of DNA fragmentation. In contrast, when a simple gel filtration column filled with SEPHAROSE CL-4B was tried, very pure fractions of intact linear BAC DNA insert were obtained in an appropriate injection buffer, e.g., 100 mM NaCl, 10 mM Tris.HCl, pH 7.5 and 0.1 mM EDTA (FIG. 5A). Unlike YAC DNA purification which typically results in a low DNA yield, the purified fractions using the SEPHAROSE CL-4B column contained a large quantity of high concentration linear DNA (e.g., 0.5 mls of 3 µg/ml DNA or more). The purified DNA could be directly visualized with ultraviolet light after ethidium bromide staining. The SEPHAROSE CL-4B column could also efficiently separate the degraded DNA (in this case in fractions 3–6) from the pure linear DNA (fractions 7–9) (FIG. 5A). Fraction 8 contained 3 µg/ml DNA and was used directly for pronuclear injection.

Figure 5B:
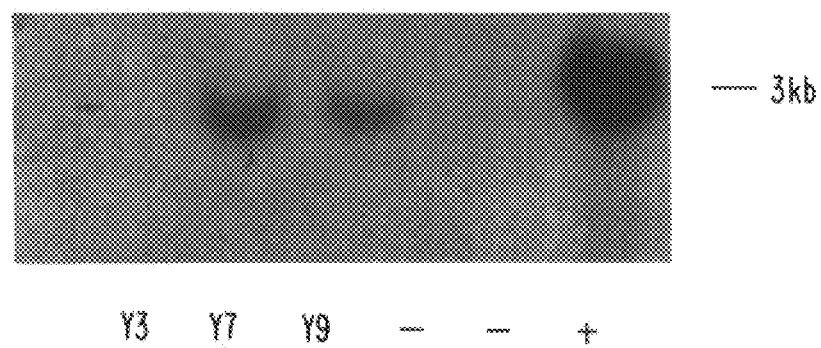

Pronuclear injection into the fertilized C57BL/6 mouse zygote is performed according to a standard protocol [Hogan et al., in *Manipulating the Mouse Embryo* (Cold Spring Harbor Laboratory Press, New York, 1986)]. Two different concentrations of fraction 8 BAC DNA (obtained as described above) were used: 3 µg/ml and 0.6 µg/ml. No newborns were obtained with the high concentration DNA, suggesting that the high concentrations may be toxic to the zygote. However, with the lower concentration of pure linear DNA, 15 newborn mice were obtained and two of them (13%), Y7 and Y9, contained the lacZ marker gene as demonstrated on a Southern blot (FIG. 5B). The intensity of the bands allows an estimate of 2–3 transgene copies for Y7 and one copy for Y9.

Figure 5C:
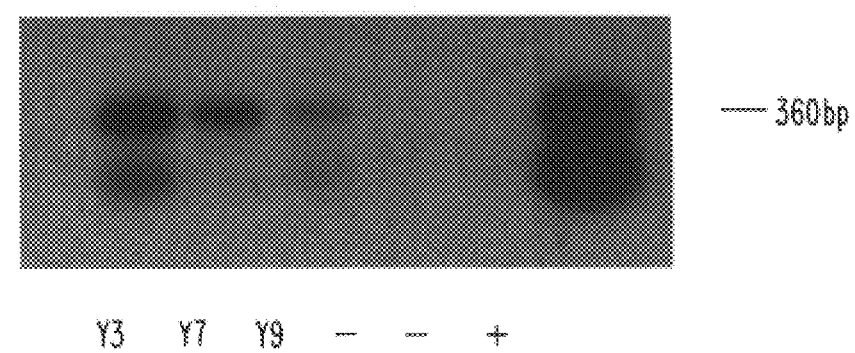
Figure 5D:
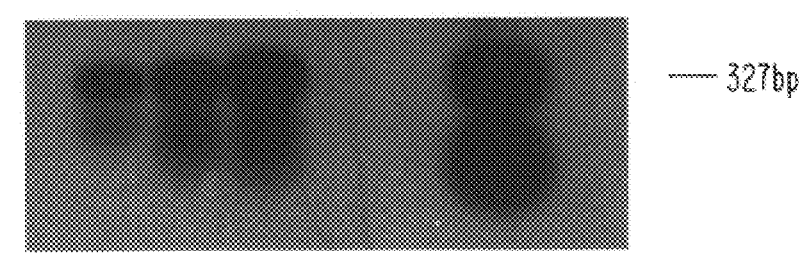

To determine if the intact BACs have been integrated into the genome, the presence of both ends of the BAC ends was assayed for in the transgenic mice. Since both BAC ends contain some vector sequence, PCR primers specific to the vector sequence were generated and used to amplify the transgenic DNA. The amplified products were then probed with a third labeled oligonucleotide probe within the amplified region. As shown in FIG. 5C and FIG. 5D: Y3, Y7 and Y9 have both ends present, while the negative controls do not. Since Y7 and Y9 also have the lacZ gene, they are likely to contain intact BAC transgenes. For Y3, whereas it has both ends it does not contain the lacZ gene. This may be due to either a rearrangement or fragmentation during the injection prior to integration.

Figure 5E:
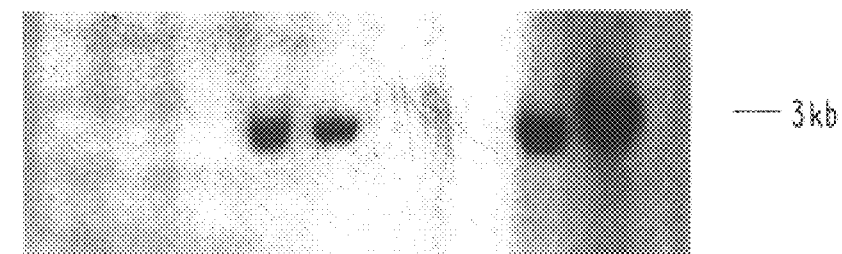

The Y7 transgenic mice also gave rise to germline transmission after breeding with B6/CBA mice. In two litters having a total of eight pups, three pups carried the LacZ transgene (FIG. 5E). Further analysis demonstrated that the transgene was transmitted in a Mendelian distribution to more than fifty Y7 offspring.

Figure 6A:
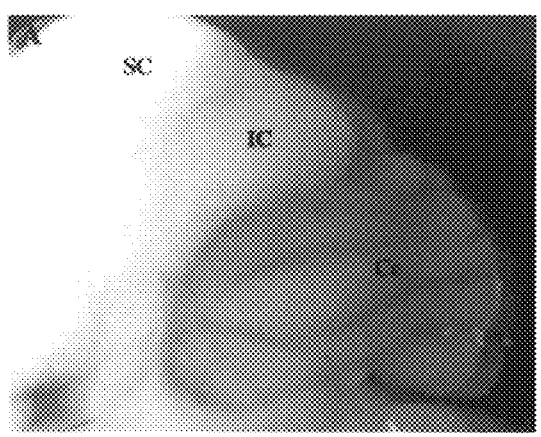
FIGS. 6A–D show the expression of the lacZ transgene in the brain of the Y7 BAC transgenic line. P6 mice brain from Y7 transgenic mice (FIG. 6A) and a wild type control litter mate (FIG. 6B) were whole mount stained to reveal lacZ expression in the Y7 cerebellum. Thick saggital sections (5 mm) from Y7 transgenic mice were also stained for lacZ expression.
Figure 6B:
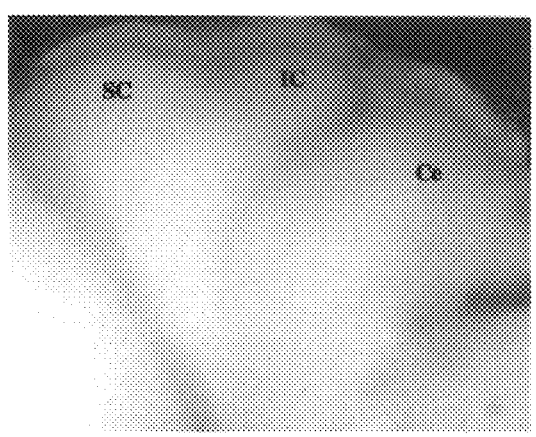
Figure 6C:
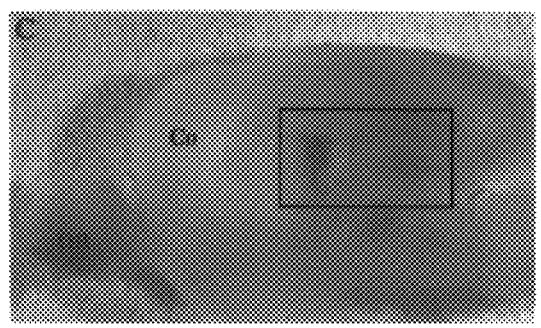
Figure 6D:
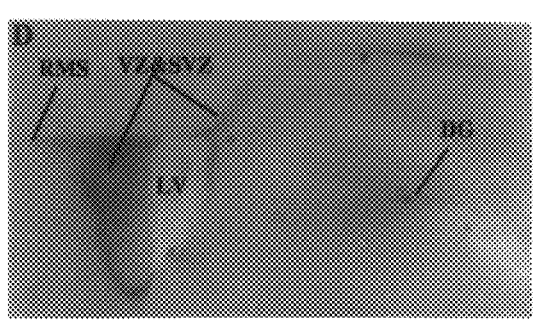

Next the expression of lacZ gene in the cerebellum of the Y7 transgenic mice was determined by whole mount lacZ staining. RU49 is normally expressed in the granule cells of the cerebellum, the dentate gyrus and the olfactory bulb (including the subventricular zone, the rostral migratory stream, and the olfactory bulb proper) [Yang et al., *Development*, 122:555–566 (1996)]. In previous studies, RU49 promoter lacZ transgenic mice with 10 kb promoter had been generated. However, all of the transgenic lines showed strong positional effects: either they did not express in the brain at all, or they were ectopically expressed in the cortex, but not the cerebellum. One particular 10 kb-lacZ transgenic line did show restricted expression in the cerebellum, however, the expression was restricted to the caudal half of the cerebellum. With 128 kb of RU49 endogenous sequence surrounding the lacZ gene in the Y7 line, at postnatal day 6, the transgenic mice showed a lacZ expression pattern closely resembling the endogenous expression pattern (FIG. 6). In the cerebellum, the marker gene is expressed throughout the cerebellum (FIG. 6A) and no expression is seen in five control littermates (FIG. 6B). Further analysis showed that the transgene is expressed at high level in the EGL and lower level in the IGL. The lacZ marker gene is also expressed in the dentate gyrus and the rostral migratory stream and the olfactory bulb (FIGS. 6C and 6D). The pattern of the BAC transgene expression closely resembles the endogenous RU49 expression pattern in the brain. It is evident that the large genomic DNA in the BAC transgene can overcome the positional effects and confer the proper expression of RU49 in vivo, in contrast to our results using conventional transgenic constructs.

As taught herein, bacterial based artificial chromosomes (BACs and PACs) are ideal for constructing large DNA for gene targeting. As demonstrated herein with the targeted BAC modification method, BACs and PACs can be readily modified to introduce selection genes, marker genes, and deletions. Making a BBPAC gene targeting construct will take about the same time as making a conventional targeting construct (1–3 months). Moreover, BBPAC targeting construct DNA can be easily isolated in milligram quantity and high quality. This is advantageous over the YAC system, since it is difficult to purify large quantities of high quality YAC DNA.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A method of selectively performing homologous recombination on a particular nucleotide sequence contained in a recombination deficient host cell comprising:
   (a) introducing a recombination cassette into the recombination deficient host cell, wherein the recombination cassette contains a nucleic acid that selectively integrates into the particular nucleotide sequence when the host cell is induced to support homologous recombination, and wherein the host cell cannot independently support homologous recombination; and
   (b) inducing the host cell to transiently support homologous recombination wherein the nucleic acid integrates into the particular nucleotide sequence; and wherein unselected nucleotide sequence rearrangements and deletions which are indicative of host cells that support homologous recombination, are not evident with a restriction endonuclease digestion map analysis with HindIII, EcoRI, XhoI, or AvrII.

2. The method of claim 1 wherein the recombination deficient host cell cannot independently support homologous recombination because the host cell is RecA$^-$; and wherein inducing the host cell to transiently support homologous recombination comprises inducing the transient expression of a RecA-like protein in the host cell.

3. The method of claim 2, wherein inducing the transient expression of the RecA-like protein is performed with a conditional replication shuttle vector that comprises a nucleotide sequence encoding a RecA-like protein; and wherein the expression of the RecA-like protein in the host cell is due to the expression of said nucleotide sequence encoding the RecA-like protein.

4. The method of claim 3 wherein the conditional replication shuttle vector is a temperature sensitive shuttle vector (TSSV) that replicates at a permissive temperature, but does not replicate at a non-permissive temperature.

5. The method of claim 4 wherein inducing the transient expression of the RecA-like protein comprises:
   (i) transforming the host cell with the TSSV at a permissive temperature, wherein said nucleotide sequence encoding the RecA-like protein is expressed in the host cell and supports the homologous recombination between the nucleic acid and the particular nucleotide sequence; and
   (ii) growing the host cell at a non-permissive temperature; wherein the TSSV encoding the RecA-like protein is diluted out.

6. The method of claim 5 wherein the permissive temperature is 30° C. and the non-permissive temperature is 43° C.

7. The method of claim 1 wherein the particular nucleotide sequence is contained in an independent origin based cloning vector (IOBCV) that is comprised by the host cell, and wherein neither the IOBCV alone, nor the IOBCV in combination with the host cell, can independently support homologous recombination.

8. The method of claim 7 wherein neither the IOBCV alone, nor the IOBCV in combination with the host cell, can independently support homologous recombination because both the IOBCV and the host cell are RecA$^-$; wherein inducing the host cell to transiently support homologous recombination comprises transiently expressing a nucleotide sequence encoding a RecA-like protein in the host cell; wherein the expression of the nucleotide sequence encoding the RecA-like protein supports homologous recombination in the host cell; and wherein inducing the transient expression of the RecA-like protein is performed with a conditional replication shuttle vector that comprises said nucleotide sequence encoding the RecA-like protein.

9. The method of claim 8 wherein the conditional replication shuttle vector is a temperature sensitive shuttle vector (TSSV) that replicates at a permissive temperature, but does not replicate at a non-permissive temperature.

10. The method of claim 2 wherein the RecA-like protein is controlled by an inducible promoter; and wherein the transient expression of the RecA-like protein is achieved by the transient induction of the inducible promoter in the host cell.

11. The method of claim 9 wherein the IOBCV is a Bacterial or Bacteriophage-Derived Artificial Chromosome (BBPAC) and the host cell is a host bacterium.

12. The method of claim 11 wherein the TSSV also contains the recombination cassette, and a first nucleotide sequence that bestows resistance to a host cell containing the TSSV against a first toxic agent, wherein said first nucleotide sequence also can be counter-selected against, and wherein the recombination cassette, said nucleotide sequence encoding the RecA-like protein, and the first nucleotide sequence are linked together on the TSSV such that when the nucleic acid integrates into the particular nucleotide sequence, said nucleotide sequence encoding the RecA-like protein and the first nucleotide sequence remain linked together, but neither said nucleotide sequence encoding the RecA-like protein nor the first nucleotide sequence remain linked to the integrated nucleic acid.

13. The method of claim 12 further comprising generating the recombination cassette by placing a first genomic fragment 5' of the nucleic acid of the recombination cassette, and placing a second genomic fragment 3' of the nucleic acid of the recombination cassette, wherein the first genomic fragment and the second genomic fragment each contain 500 or more basepairs of the particular nucleotide sequence, and wherein the first genomic fragment corresponds to a region of the particular nucleotide sequence that is 5' to the region of the particular nucleotide sequence that corresponds to the second genomic sequence.

14. The method of claim 13 wherein the BBPAC contains a second nucleotide sequence that bestows resistance to the host cell against a second toxic agent; and
   wherein introducing the recombination cassette into the host cells is performed by transforming the host cells with the TSSV; and wherein inducing the transient expression of the RecA-like protein to support homologous recombination comprises:
   (i) incubating the host cells at a permissive temperature in the presence of the first toxic agent and the second toxic agent, wherein transformed host cells containing the TSSV and the BBPAC are selected for; and wherein the RecA-like protein is expressed and a first homologous recombination event occurs between the recombination cassette and the particular nucleotide sequence forming a co-integrate between the TSSV and the BBPAC; wherein a TSSV is either free or part of a co-integrate;
   (ii) incubating the transformed host cells at a non-permissive temperature in the presence of the first toxic agent and the second toxic agent, wherein host cells containing a TSSV co-integrate are selected for, and wherein free TSSV cannot replicate;
   (iii) selecting a host cell containing a co-integrate between the TSSV and the BBPAC by Southern analysis;
   (iv) incubating the host cells containing a co-integrate between the TSSV and the BBPAC at a non-permissive temperature in the presence of the second toxic agent, wherein a second homologous recombination event occurs between the recombination cassette and the particular nucleotide sequence, therein integrating the nucleic acid into the particular nucleotide sequence and forming a resolved BBPAC in the host cell; and
   (v) incubating the host cells containing the resolved BBPAC in the presence of the second toxic agent, and a counter-selecting agent; wherein the counter-selecting agent is toxic to host cells containing the first nucleotide sequence and whereby host cells containing said nucleotide sequence encoding the RecA-like protein are removed.

15. The method of claim 14 wherein the permissive temperature is 30° C., and the non-permissive temperature is 43° C.

16. The method of claim 14 further comprising selecting a host cell containing a resolved BBPAC by colony hybridization with a labeled probe that binds to the nucleic acid, or a protein encoded by the nucleic acid.

17. The method of claim 14 wherein the first nucleotide sequence confers tetracycline resistance and wherein the counter-selecting agent is fusaric acid.

18. The method of claim 14 wherein the RecA-like protein is recA.

19. The method of claim 18 wherein the TSSV is pSV1.RecA having the ATCC no. 97968.

20. The method of claim 8 wherein the RecA-like protein is controlled by an inducible promoter; and wherein the transient expression of the RecA-like protein is achieved by the transient induction of the inducible promoter in the host cell.

21. The method of claim 20 wherein the IOBCV is a BBPAC and the recombination deficient host cell is a bacterium.

22. The method of claim 21 wherein the bacterium is an *E. coli.* bacterium.

23. The method of claim 21 wherein the RecA-like protein is recA.

24. A conditional replication shuttle vector that encodes a RecA-like protein.

25. The conditional replication shuttle vector of claim 24 that is a temperature sensitive shuttle vector (TSSV).

26. The TSSV of claim 25 which contains a nucleotide sequence that can be counter-selected against.

27. The TSSV of claim 26 wherein the nucleotide sequence confers tetracycline resistance.

28. The TSSV of claim 26 wherein the RecA-like protein is recA.

29. The TSSV of claim 28 that is pSV1.RecA having the ATCC no. 97968.

30. An independent origin based cloning vector that contains a nucleic acid that has been directly modified with specificity by having undergone homologous recombination with a conditional replication shuttle vector in a RecA⁻ host cell, wherein the conditional replication shuttle vector encodes a RecA-like protein.

31. The independent origin based cloning vector of claim 30 which is a BBPAC.

32. The BBPAC of claim 31 wherein the conditional replication shuttle vector is a TSSV.

33. The BBPAC of claim 32 wherein the TSSV is pSV1.RecA having the ATCC no. 97968.

34. A kit for performing homologous recombination in a BBPAC comprising:
   (a) a conditional replication shuttle vector;
   (b) a building vector;
   (c) a restriction map for the shuttle vector; and
   (d) a restriction map for the building vector.

35. The kit of claim 34 further comprising a protocol for using the contents of the kit to perform homologous recombination.

36. A kit for performing homologous recombination in a BBPAC comprising:
   (a) the pSV1.RecA temperature-sensitive shuttle vector; and
   (b) a building vector selected from the group consisting of pBV.IRES.LacZ.PA; pBV.EGFP1; pBV.IRES.EGFP1; and pBV.pGK.Neo.PA.

37. The kit of claim 36 further comprising:
   (c) a restriction map for pSV1.RecA; and
   (d) a restriction map for the building vector.

38. The kit of claim 36 further comprising a protocol for using the contents of the kit to perform homologous recombination.

39. The method of claim 16 wherein the nucleic acid that binds to the labeled probe is selected from the group consisting of a RNA and a DNA.

40. The method of claim 7 wherein the IOBCV is a Bacterial or Bacteriophage-Derived Artificial Chromosome (BBPAC) and the host cell is a host bacterium.

41. The method of claim 40 wherein the BBPAC is a BAC.

42. The method of claim 40 wherein the BBPAC is PAC.

43. The method of claim 7 wherein neither the IOBCV alone, nor the IOBCV in combination with the host cell, can independently support homologous recombination because both the IOBCV and the host cell are RecA$^-$; wherein inducing the host cell to transiently support homologous recombination comprises transiently expressing a nucleotide sequence encoding a protein that can support homologous recombination in the host cell; wherein the expression of the nucleotide sequence encoding the protein supports homologous recombination in the host cell; and wherein inducing the transient expression of the protein is performed with a conditional replication shuttle vector that comprises said nucleotide sequence encoding the protein.

44. The method of claim 43 wherein the IOBCV is a Bacterial or Bacteriophage-Derived Artificial Chromosome (BBPAC) and the host cell is a host bacterium.

45. The method of claim 44 wherein the BBPAC is a BAC.

46. The method of claim 44 wherein the BBPAC is a PAC.

47. An independent origin based cloning vector that contains a nucleic acid that has been directly modified with specificity by having undergone homologous recombination with a conditional replication shuttle vector in a RecA$^-$ host bacterial cell, wherein the conditonal replication shuttle vector encodes a protein that can support homologous recombination in the RecA$^-$ host bacterial cell.

48. The independent origin based cloning vector of claim 47 which is a BBPAC.

49. The method of claim 48 wherein the BBPAC is a BAC.

50. The method of claim 48 wherein the BBPAC is a PAC.

* * * * *

UNITED STATES PATENT AND TRADEMARK OFFICE
CERTIFICATE OF CORRECTION

PATENT NO. : 6,143,566
DATED : November 7, 2000
INVENTOR(S) : Nathaniel Heintz; Peter Model; and Xiangdong W. Yang It is certified that error appears in the above-identified patent and that said Letters Patent is hereby corrected as shown below:

On the title page, item [73]:

Please change the Assignee from "The Rockfeller University"
to read
--The Rockefeller University--.

Signed and Sealed this

Twenty-ninth Day of May, 2001

Attest:

NICHOLAS P. GODICI

Attesting Officer

Acting Director of the United States Patent and Trademark Office